US007206065B2

(12) United States Patent
Anderson et al.

(10) Patent No.: US 7,206,065 B2
(45) Date of Patent: Apr. 17, 2007

(54) METHODS AND APPARATUS FOR AUTOMATION OF THE TESTING AND MEASUREMENT OF OPTICAL FIBER

(75) Inventors: Erling R. Anderson, Wilmington, NC (US); Richard E. Blazek, Wilmington, NC (US); William J. Kish, Wilmington, NC (US)

(73) Assignee: Corning Incorporated, Corning, NY (US)

( * ) Notice: Subject to any disclaimer, the term of this patent is extended or adjusted under 35 U.S.C. 154(b) by 0 days.

(21) Appl. No.: 11/394,953

(22) Filed: Mar. 31, 2006

(65) Prior Publication Data

US 2006/0181696 A1 Aug. 17, 2006

Related U.S. Application Data

(62) Division of application No. 09/713,454, filed on Nov. 15, 2000, now Pat. No. 7,053,995.

(60) Provisional application No. 60/166,015, filed on Nov. 17, 1999, provisional application No. 60/168,111, filed on Nov. 30, 1999.

(51) Int. Cl.
*G01N 21/00* (2006.01)
(52) U.S. Cl. .................................. 356/73.1
(58) Field of Classification Search ..................... None
See application file for complete search history.

(56) References Cited

U.S. PATENT DOCUMENTS

| 4,662,743 A | 5/1987 | Nishimura et al. ........ 356/73.1 |
| 4,676,635 A | 6/1987 | Sakamoto et al. ......... 356/73.1 |
| 4,882,497 A | 11/1989 | Inoue et al. ................. 250/560 |
| 4,990,770 A | 2/1991 | Hemmann et al. ..... 250/227.24 |
| 5,119,546 A | 6/1992 | Cameron et al. ............. 29/748 |
| 5,253,035 A | 10/1993 | Fukuoka et al. ........... 356/73.1 |
| 5,258,613 A | 11/1993 | Okada et al. .......... 250/227.11 |

(Continued)

FOREIGN PATENT DOCUMENTS

| DE | 2429810 A1 | 1/1976 |
| DE | 39 10 503 A1 | 10/1990 |
| DE | 3910503 A1 | 10/1990 |
| EP | 0 179 183 A2 | 4/1986 |
| WO | WO 91/13837 | 9/1991 |
| WO | WO 00/40495 | 7/2000 |
| WO | WO 00/58707 | 10/2000 |

OTHER PUBLICATIONS

Yamashita et al, "Automated Optical Fiber Test Systems", International Wire & Cable Symposium Proceedings 1988, pp. 230-235.

*Primary Examiner*—Tu T. Nguyen
(74) *Attorney, Agent, or Firm*—Robert L. Carlson

(57) ABSTRACT

A system and methods for automating the testing of optical fiber are described. According to one aspect of the present invention, an automated conveyor system moves spools of optical fiber contained on pallets from testing station to testing station. According to another aspect of the present invention, a single spool is carried by a specially designed pallet. According to another aspect of present invention, an apparatus automatically strips, cleans, and cleaves the fiber ends once the spool reaches the apparatus. The fiber ends are then automatically manipulated into the appropriate location for a predetermined test to be performed. According to another aspect of the invention, an apparatus automatically acquires a sample length of the optical fiber and strips, cleans, and cleaves the fiber ends of the sample. The sample length of the optical fiber is then manipulated into the appropriate location for a second predetermined test to be performed.

12 Claims, 20 Drawing Sheets

U.S. PATENT DOCUMENTS

| | | | |
|---|---|---|---|
| 5,301,884 A | 4/1994 | Horneman | 242/7.09 |
| 5,394,606 A | 3/1995 | Kinoshita et al. | 29/705 |
| 5,441,215 A | 8/1995 | Nagayama et al. | 242/580 |
| 5,529,186 A * | 6/1996 | Bass | 206/395 |
| 5,871,559 A | 2/1999 | Bloom | 65/501 |

* cited by examiner

TO FIG. 11C

METHODS AND APPARATUS FOR AUTOMATION OF THE TESTING AND MEASUREMENT OF OPTICAL FIBER

This application is a divisional of U.S. application Ser. No. 09/713,454, now U.S. Pat. No. 7,053,995 filed on Nov. 15, 2000, which claims the benefit of priority of U.S. Provisional Patent Application Ser. No. 60/166,015, filed on Nov. 17, 1999 and U.S. Provisional Patent Application Ser. No. 60/168,111 filed on Nov. 30, 1999, the content of which is relied upon and incorporated herein by reference in its entirety, and the benefit of priority under 35 U.S.C. § 120 is hereby claimed.

FIELD OF THE INVENTION

The present invention relates generally to improvements in the manufacture of optical fiber. More specifically, the present invention relates to methods and apparatus for automating the testing of optical fiber wound onto a spool.

BACKGROUND OF THE INVENTION

In the current manufacturing process for optical fiber, optical fiber is typically wound onto a spool for measurement and testing, shipping to a customer, and subsequent processing at the customer's facility. The measurement and testing of optical fiber is currently performed manually by multiple technicians, with carts carrying a number of spools being manually moved from test station to test station. At a test station a technician removes a spool from the cart and places the spool on a measurement rack. The technician then strips and removes the plastic fiber coating from both ends of the optical fiber, cleaning off excess coating and any remaining debris. The fiber ends are manipulated by the technician into a cleaver and cut. Next, the technician loads the fiber ends into a computer controlled measurement system and initiates a measurement sequence to test at least one characteristic of the optical fiber, e.g., fiber cutoff wavelength, attenuation, fiber curl, cladding diameter, or coating diameter. The fiber is then removed from the testing system and the spool returned to the cart. All of the spools on the cart or only selected spools may be tested as desired. The cart is then manually moved to the next test station for another series of tests. The amount of manual labor involved results in high labor costs and higher manufacturing costs for optical fiber.

Accordingly, it would be highly advantageous to further automate the manual steps of optical fiber measurement and testing, reducing the time required in the measurement and testing area and thus reducing the cost of manufacturing optical fiber and providing faster feedback on the manufacturing process. Additionally, it would be highly advantageous to provide methods and apparatus for the automated testing of optical fiber which reduces the opportunity for human error and provides a more repeatable process.

SUMMARY OF THE INVENTION

The present invention provides advantageous methods and apparatus for the automation of the testing of optical fiber. The present invention includes an automated conveyor system which moves spools of optical fiber contained on pallets from testing station to testing station. According to one aspect of the present invention, a single spool is carried by a specially designed pallet which has a number of advantageous features described further below. According to another aspect of present invention, an apparatus automatically strips, cleans, and cleaves the fiber ends once the spool reaches the apparatus. The fiber ends are then automatically manipulated into the appropriate location for a predetermined test to be performed. According to another aspect of the invention, an apparatus automatically acquires a sample length of the optical fiber and strips, cleans, and cleaves the fiber ends of the sample. The sample length of the optical fiber is then manipulated into the appropriate location for a second predetermined test to be performed.

These and other features, aspects and advantages of the invention will be apparent to those skilled in the art from the following detailed description taken together with the accompanying drawings.

DETAILED DESCRIPTION

The present invention now will be described more fully with reference to the accompanying drawings, in which several currently preferred embodiments of the invention are shown. However, this invention may be embodied in various forms and should not be construed as limited to the exemplary embodiments set forth herein. Rather, these representative embodiments are described in detail so that this disclosure will be thorough and complete, and will fully convey the scope, structure, operation, functionality, and potential of applicability of the invention to those skilled in the art.

Figure 1:
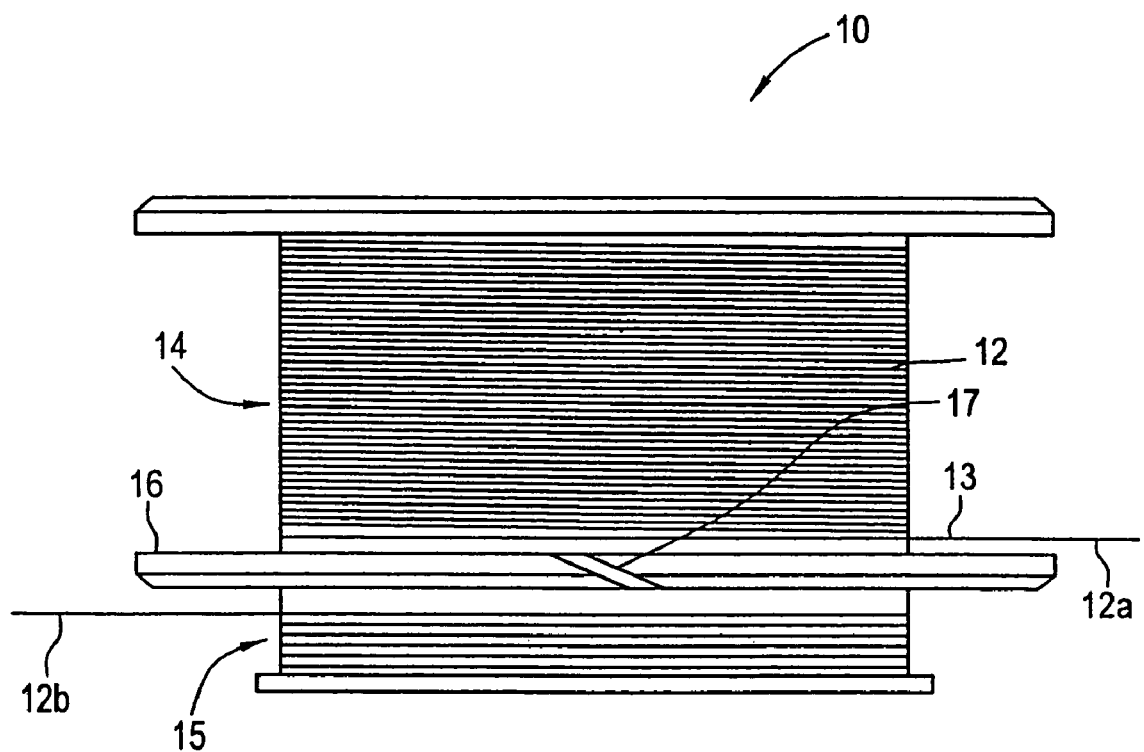
FIG. 1 shows a view of a spool which may suitably be used in conjunction with the present invention.

Referring to the drawings, FIG. 1 shows a top view of a spool 10 which may be advantageously used in conjunction with the present invention. The spool 10 comprises a primary barrel 14 and a lead meter barrel 15 separated from each other by an outboard flange 16. A length of optical fiber 12 has been wound onto the primary barrel 14 and the lead meter barrel 15 during the manufacturing process. In a presently preferred embodiment, spool 10 may be, for example, a "single" spool, having 25 km of optical fiber wound onto the primary barrel 14, or a "double" spool containing 50 km of optical fiber wound onto the primary barrel 14. A short length of the optical fiber 12 has been wound onto the lead meter barrel 15. The outboard flange 16 has a slot 17 providing a path for the optical fiber 12 between the lead meter barrel 15 and the primary barrel 14. As seen from the top view of FIG. 1, an outer end 12a of the optical fiber 12 extends from the underside of the primary barrel 14 and an inner end 12b extends from the underside of the lead meter barrel 15. The optical fiber 12 also typically includes a plastic coating 13. Further details of a presently preferred spool 10 for use in conjunction with the present invention are provided in U.S. patent application Ser. No. 60/115,540, filed on Jan. 12, 1999, entitled "System And Methods For Providing Under-Wrap Access To Optical Fiber Wound Onto Spools" which is incorporated by reference herein in its entirety.

Figure 2:
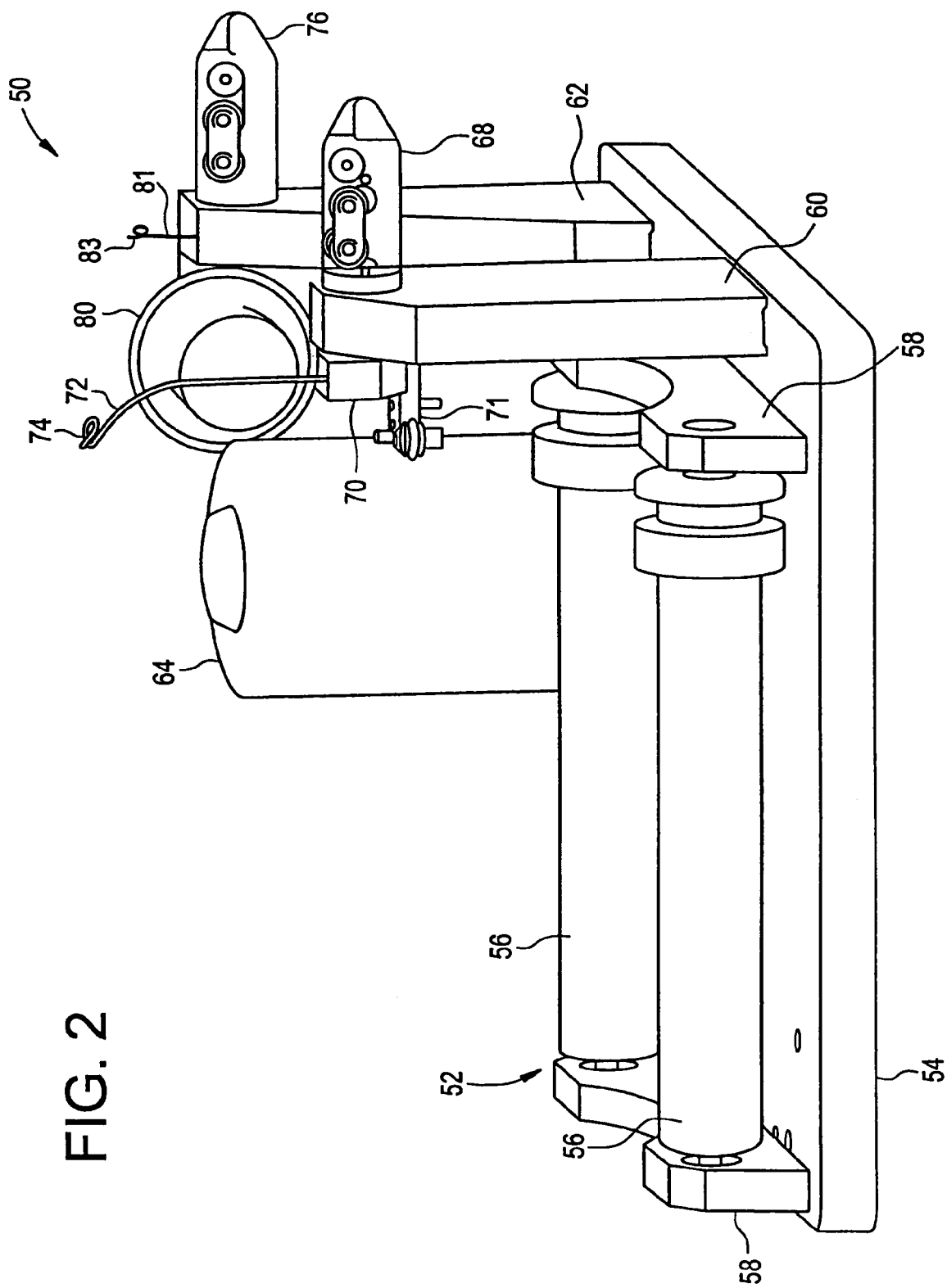
FIG. 2 shows an isometric view of a pallet in accordance with the present invention.

FIG. 2 shows an isometric view of a pallet 50 in accordance with a first embodiment of the present invention. The pallet 50 is adapted to carry the spool 10 of optical fiber 12 such that the fiber ends 12a and 12b are available to the testing equipment of automated fiber measurement system 100 described below. The pallet 50 includes a roller assembly 52 mounted on a base 54 adapted for carrying the spool 10. The roller assembly 52 includes a pair of rollers 56 and a pair of base plates 58. Also mounted on the base 54 are vertical brackets 60 and 62, and an upright guide roller 64.

Figure 3A:
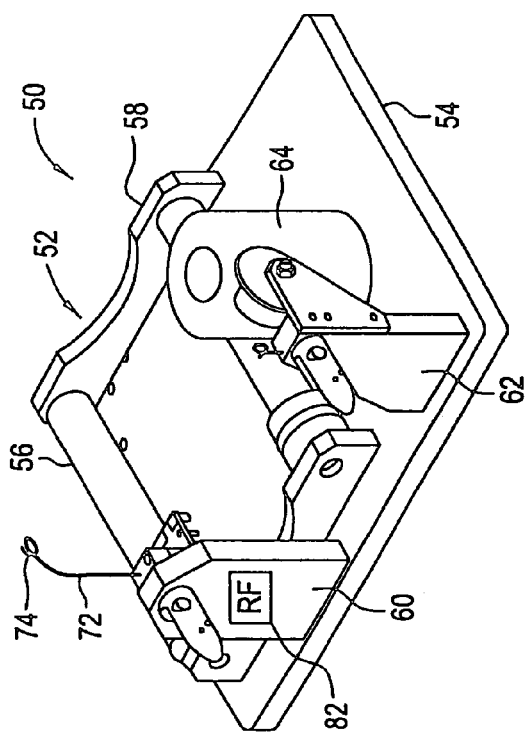
FIGS. 3A, 3B, 3C, and 3D show, respectively, top, front, side, and isometric views of a pallet in accordance with the present invention.
Figure 3D:
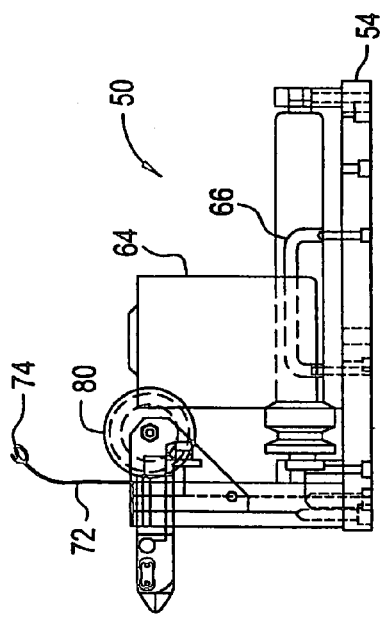
Figure 3B:
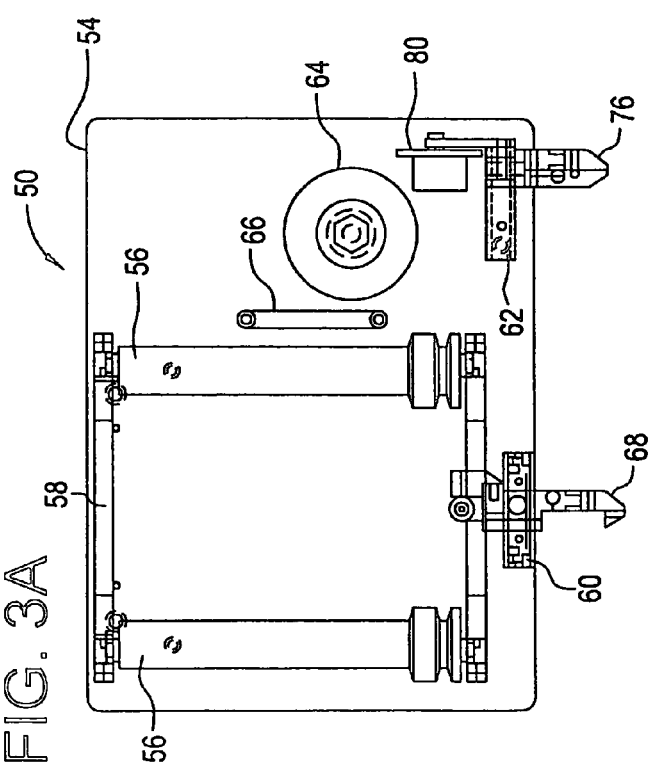
Figure 3C:
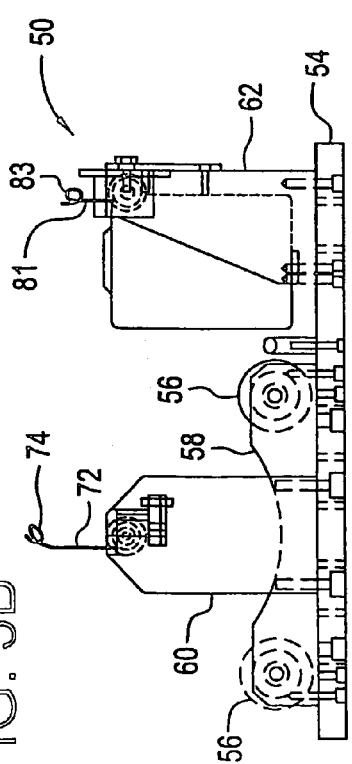
Figure 4:
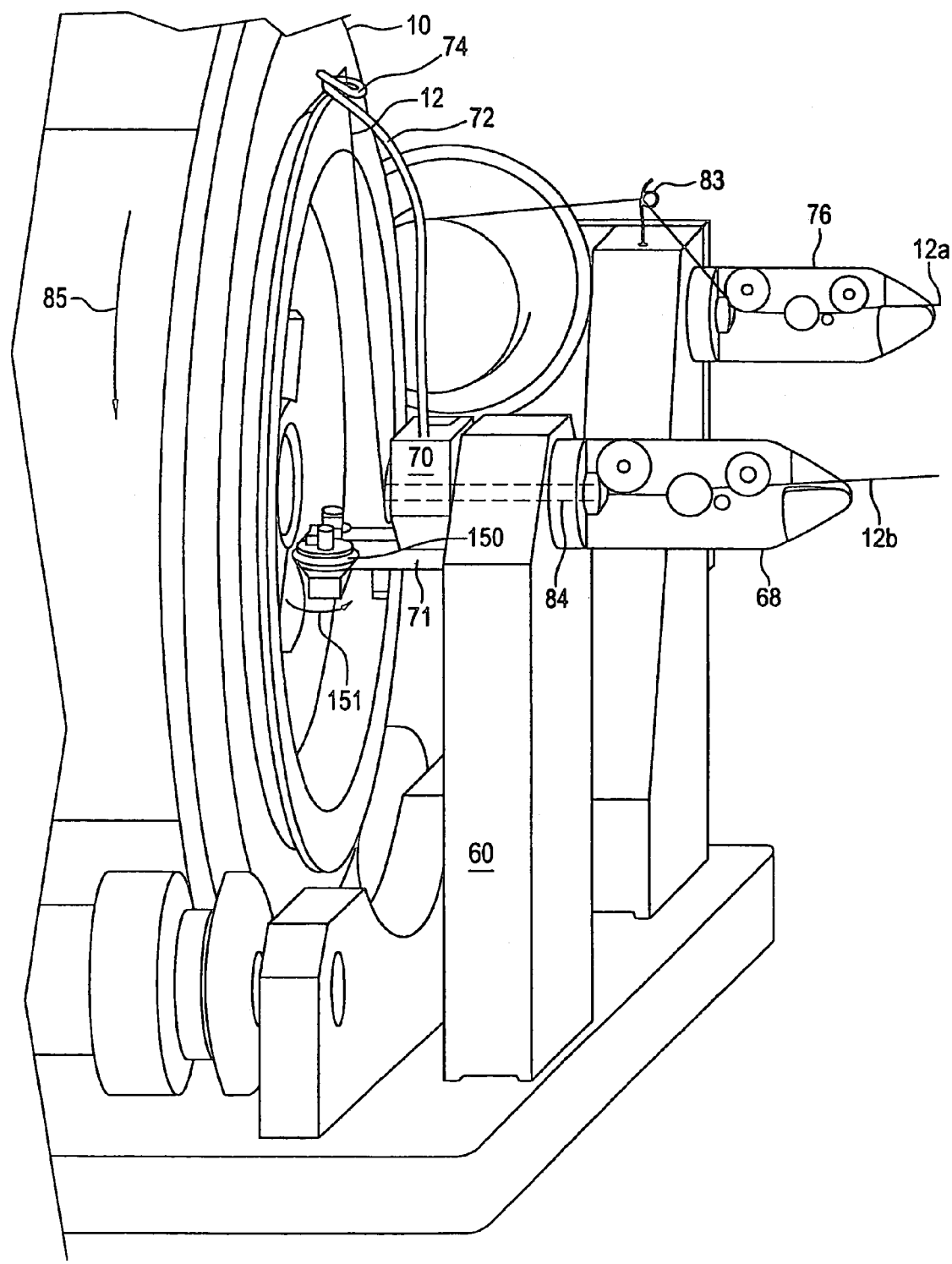
FIG. 4 shows an isometric view of the pallet of FIG. 2 carrying the spool of FIG. 1.

As shown in FIGS. 3A and 3C, a guide bar 66 is mounted to the base 54. A feed finger assembly 68, a pickoff assembly 70, and a clutch assembly 71 are rotationally mounted on the vertical bracket 60. Mounted to the pickoff assembly 70 is a fiber guide 72 which includes an eyelet 74. A feed finger assembly 76, a guide roller 80, and a fiberguide 81 including an eyelet 83 are mounted on the vertical bracket 62. As best seen in FIG. 4, a center hole 84 extends through the rotational center of the feed finger assembly 68, the pickoff assembly 70, and the vertical bracket 60.

As shown in FIG. 3D, a radio frequency (RF) identification tag 82 identifying the spool 10 is attached to the vertical bracket 60. In addition to identifying the spool 10, the RF tag 82 is capable of storing information which has been written to it, allowing the RF tag 82 to provide a travelling database for the spool 10 as it passes through the system 100. The RF tag 82 provides processing instructions for individual test stations and stores the data of the test results. As each spool 10 is processed by the individual test stations of the system 100, the results of each of the tests are written to the RF tag 82. Thus, when the spool 10 has been processed by each of the appropriate test stations, the RF tag 82 contains the test results of all the tests performed. Additionally, the RF tag 82 also contains the routing instructions for the spool 10, indicating which test stations need to process the spool 10.

FIG. 4 shows a view of the pallet 50 carrying the spool 10. To load the spool 10 onto the pallet 50, an operator manually places the spool 10 on the rollers 56 and feeds the inner end 12b of the optical fiber from lead meter barrel 15 through the eyelet 74, center hole 84 and feed finger assembly 68 such that the end 12b extends outward from the feed finger assembly 68. The outer end 12a of the optical fiber from primary barrel 14 is first fed around the guide roller 64, over guide roller 80, and then fed through the eyelet 83 and feed finger assembly 76 such that the outer end 12a extends outward from the feed finger assembly 76. Thus, as shown in FIG. 4, the pallet 50 provides convenient access to the ends 12a and 12b of the optical fiber for both automated and manual test equipment.

Furthermore, the spool 10 and pallet 50 advantageously allow the optical fiber 12 to be unwound from either the inner end 12b or the outer end 12a individually, or both the inner end 12b and outer end 12a simultaneously, without causing the opposite end to be disturbed. This allows both automated and manual test equipment to readily acquire samples of optical fiber from either or both of the fiber ends 12a and 12b. The fiber ends 12a and 12b may also be readily engaged and pulled or directed to test stations, allowing the optical fiber 12 to be tested while wound onto the spool 10.

The clutch mechanism 71 includes at least a single wheel 150 that is forced into contact with the spool 10. The wheel 150 on clutch mechanism 71 rotates in a single direction which enables fiber to be pulled from fiber end 12b, in this case the direction indicated by arrow 151. As optical fiber 12 is unwound from the outer end 12a, the spool 10 rotates in a counter-clockwise direction (as indicated by arrow 85 in FIG. 4), dispensing the optical fiber 12. Because the wheel 150 of clutch assembly 71 does not rotate in a direction which is counter to the direction indicated by arrow 151, the force caused by the counterclockwise rotation of spool 10 causes the entire clutch assembly 71, pickoff assembly 70, and feed finger assembly 68 to rotate counter-clockwise around the axis of center hole 84 of feed finger assembly 68. This rotation keeps the inner end 12b of optical fiber 12 from being removed from the spool 10. As the outer end 12a of optical fiber 12 is unwound from the spool, the tension on the inner end 12b of the optical fiber 12 held by the fiber guide eyelet 74 exerts a counter-clockwise force on the fiber guide 74, causing the clutch assembly 71, the pickoff assembly 70, and the feed finger assembly 68 to rotate in synchronization with the spool 10. In other words, as the spool 10 is rotated counter-clockwise by optical fiber 12 being unwound from the outer end 12a, the optical fiber 12 extending from the spool 10 through the eyelet 74 of fiber guide 72 pulls the clutch assembly 71, the pickoff assembly 70, and the feed finger assembly 68 along with the rotating spool 10.

As optical fiber 12 is unwound from the inner end 12b, the clutch assembly 71, the pickoff assembly 70 and the feed finger assembly 68 rotate counter-clockwise (as indicated by the arrow 85) , causing wheel 150 to rotate in the direction indicated by arrow 151, to thereby remove optical fiber 12 from the lead meter barrel 15 while the spool 10 remains fixed, preventing optical fiber 12 from unwinding from the spool 10 on the outer end 12a. The weight of the spool 10 prevents the spool 10 from rotating as the fiber 12 is unwound from the inner end 12b. The tension caused by the optical fiber 12 being pulled through fiber guide eyelet 74 exerts a counter-clockwise force on fiber guide 72, and thus clutch assembly 71, the pickoff assembly 70, and the feed finger assembly 68, causing these elements to rotate in a counterclockwise direction as the optical fiber 12 is pulled through the feed finger assembly 68.

Alternatively, fiber can be removed from spool 10 simultaneously by simply pulling on both ends of fiber at the same time.

Figure 5:
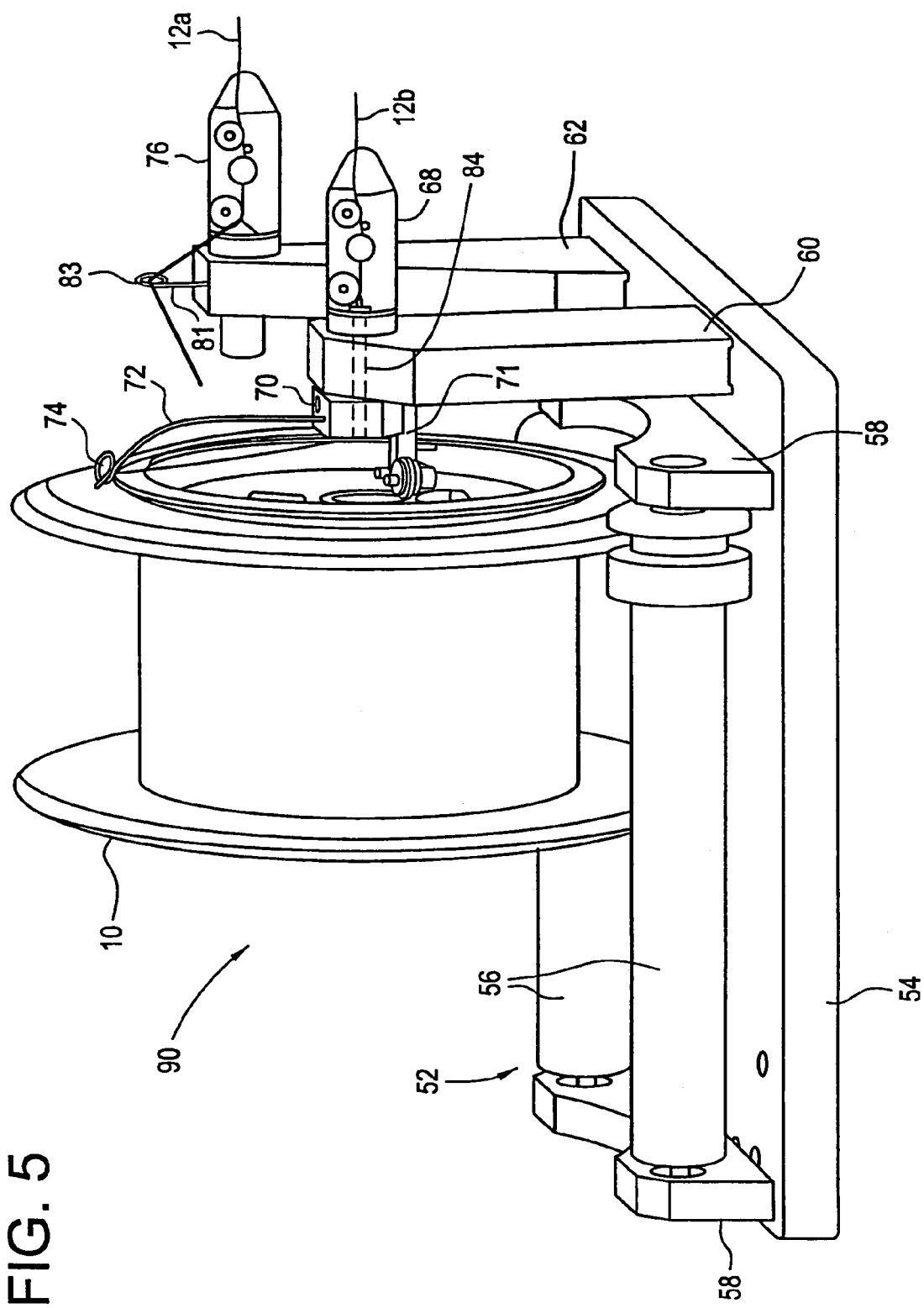
FIG. 5 shows an isometric view of a pallet in accordance with another aspect of the present invention carrying the spool of FIG. 1.
Figure 6:
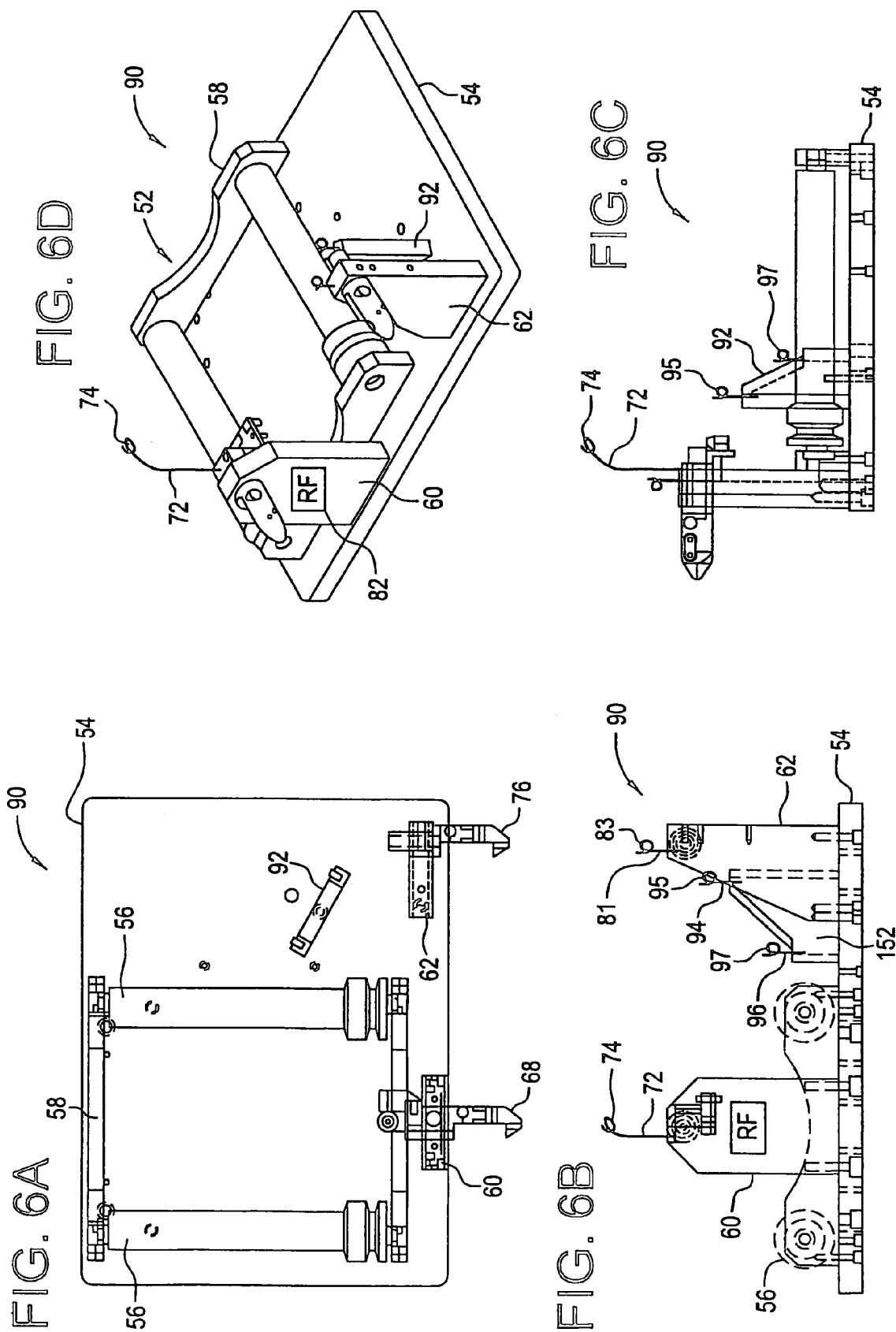
FIGS. 6A, 6B, 6C, and 6D show, respectively, top, front, side, and isometric views of the pallet of FIG. 5.

FIG. 5 shows an isometric view of a pallet 90 in accordance with a second embodiment of the present invention. Since many components are arranged in the same manner as the first embodiment, like reference numerals are used to designate elements common to the two embodiments. The pallet 90 is adapted to carry the spool 10 of optical fiber 12 such that the fiber ends 12a and 12b are available to the testing equipment of system 20 described above. The pallet 90 includes a roller assembly 52 mounted on a base 54 adapted for carrying the spool 10. The roller assembly 52 includes a pair of rollers 56 and a pair of base plates 58. Mounted on the base 54 are vertical brackets 60 and 62. As best seen in FIGS. 6A and 6C, a vertical bracket 92 is also mounted on the base 54. As shown in FIG. 5, a feed finger assembly 68, a pickoff assembly 70, and a clutch assembly 71 are rotationally mounted on the vertical bracket 60. Mounted to the pickoff assembly 70 is a fiber guide 72 which includes an eyelet 74. A feed finger assembly 76 and a fiber guide 81 including an eyelet 83 are mounted on the vertical bracket 62. As best seen in FIG. 6B, a fiber guide 94 including an eyelet 95 and a fiber guide 96 including an eyelet 97 are mounted on the vertical bracket 92. A center hole 84 extends through the rotational center of the feed finger assembly 68, the pickoff assembly 70, and the vertical bracket 60.

As shown in FIG. 6D, a radio frequency (RF) identification tag 82 identifying the spool 10 is attached to the vertical bracket 60. In addition to identifying the spool 10, the RF tag 82 is capable of storing information which has been written to it, allowing the RF tag 82 to provide a traveling database for the spool 10 as it passes through the system 20. The RF tag 82 provides processing instructions for individual test stations and stores the data of the test results. As each spool 10 is processed by the individual test stations of the system 20, the results of the tests are written to the RF tag 82. The RF tag 82 also contains the routing instructions for the spool 10, indicating which test stations need to process the spool 10.

Figure 7:
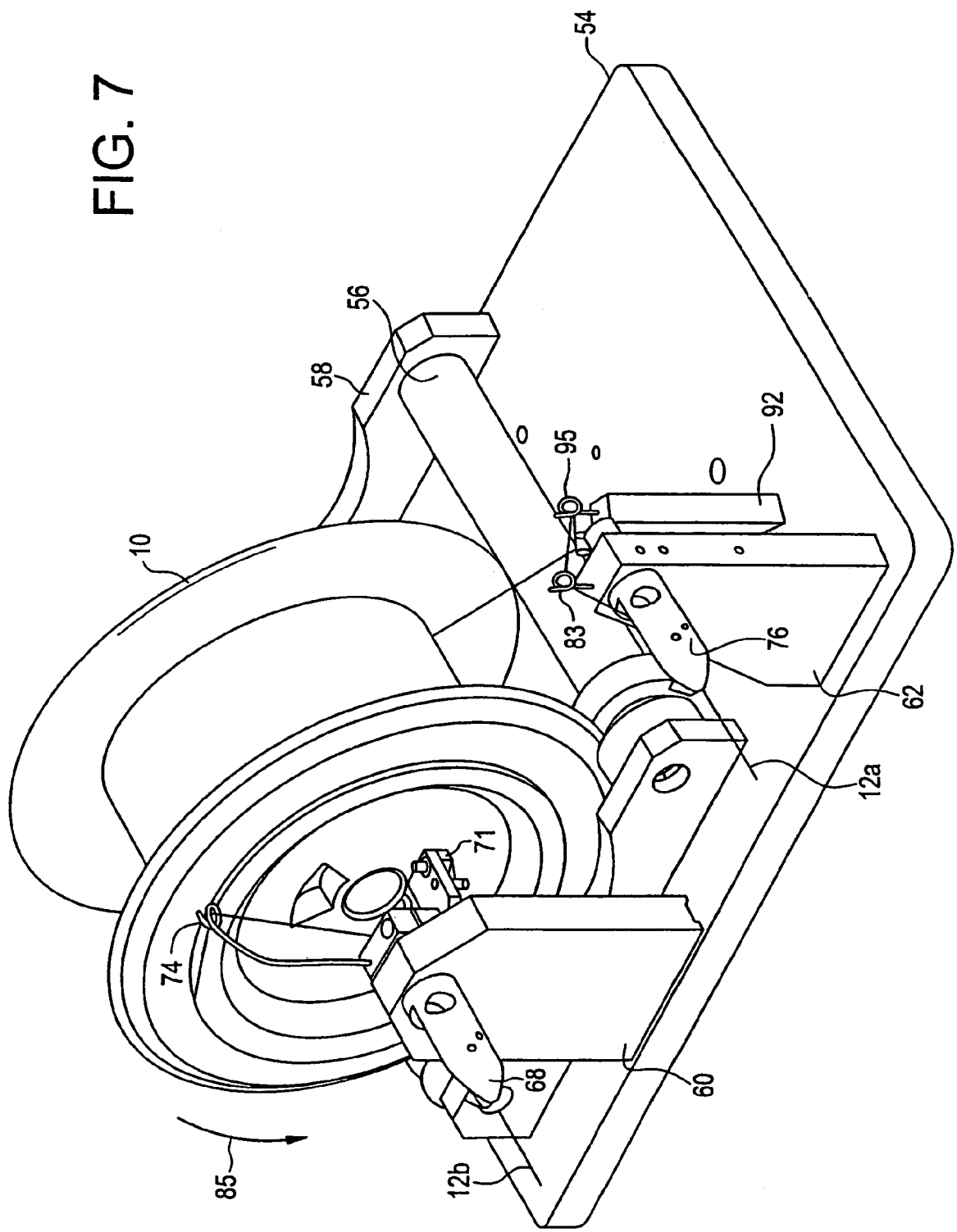
FIG. 7 shows an isometric view of the pallet of FIG. 5 carrying the spool of FIG. 1.

FIG. 7 shows a view of the pallet 90 carrying the spool 10. To load the spool 10 onto the pallet 90, an operator manually places the spool 10 on the rollers 56 and feeds the inner end 12b of the optical fiber through the eyelet 74, center hole 84 and feed finger assembly 68 such that the end 12b extends outward from the feed finger assembly 68. The outer end 12a of the optical fiber is fed through the eyelets 97, 95 and 83, in respective order, and then fed through the feed finger assembly 76 such that the end 12a extends outward from the feed finger assembly 76. Thus, as shown in FIGS. 5 and 7, the pallet 90 provides convenient access to the fiber ends 12a and 12b of the optical fiber for both automated and manual test equipment.

Furthermore, the spool 10 and pallet 90 advantageously allow the optical fiber 12 to be unwound from either the inner end 12b or the outer end 12a, or both the inner end 12b and the outer end 12a simultaneously, without causing the opposite end to be disturbed. As optical fiber is unwound from the outer end 12a, the spool rotates in a counter-clockwise direction (as indicated by arrow 85 in FIG. 7), dispensing the optical fiber. While the spool is rotating counter-clockwise, the clutch assembly 71, the pickoff assembly 70 and the feed finger assembly 68 also rotate counter-clockwise, preventing optical fiber 12 from pulling out of the feed finger assembly 68. As the optical fiber 12 is unwound from the outer end 12a, the tension on the inner end 12b of the optical fiber 12 held by the fiber guide 74 exerts a counter-clockwise force on the fiber guide 74, causing the clutch assembly 71, the pickoff assembly 70, and the feed finger assembly 68 to rotate in synchronization with the spool 10. In other words, as the spool 10 is rotated counter-clockwise by optical fiber 12 being unwound from the outer end 12a, the optical fiber 12 extending from the spool 10 through the fiber guide 74 pulls the clutch assembly 71, the pickoff assembly 70, and the feed finger assembly 68 along with the rotating spool 10.

As optical fiber 12 is unwound from the inner end 12b, the clutch assembly 71, the pickoff assembly 70 and the feed finger assembly 68 rotate counter-clockwise to remove optical fiber 12 from the lead meter barrel 15 while the spool 10 remains fixed, preventing optical fiber 12 from unwinding from the spool 10 on the outer end 12a The tension on the optical fiber 12 held by the fiber guide 74 exerts a counter-clockwise (as indicated by the arrow 85) force on the clutch assembly 71, the pickoff assembly 70, and the feed finger assembly 68, causing these elements to rotate counter-clockwise as the optical fiber 12 is pulled through the feed finger assembly 68. The weight of the spool 10 prevents the spool 10 from rotating as the fiber 12 is unwound from the inner end 12b.

Figure 8:
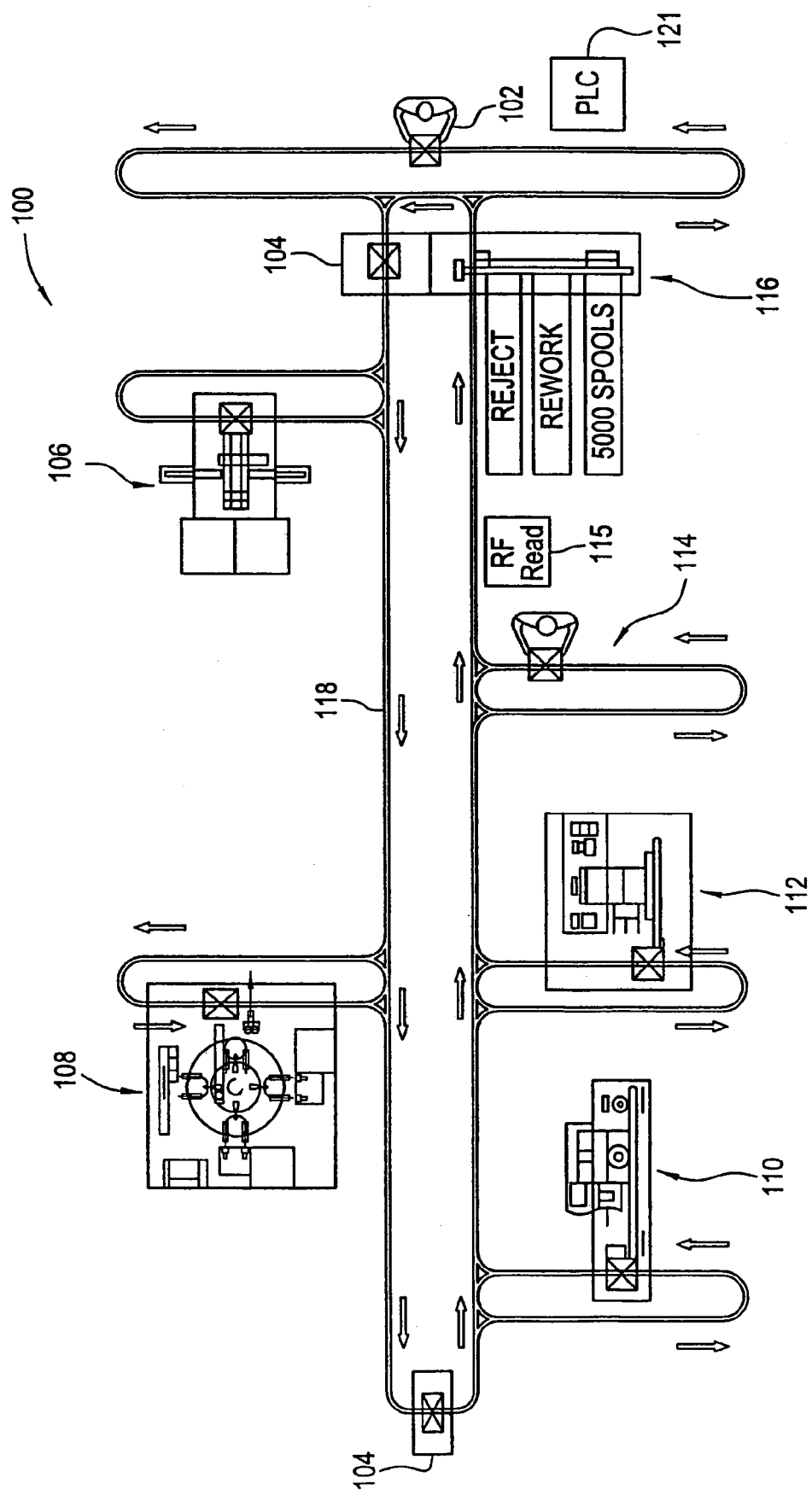
FIG. 8 is an overall view of an automated optical fiber testing system in accordance with the present invention.

FIG. 8 shows an overall view of an automated optical fiber measurement system 100 in accordance with the present invention. The system 100 may suitably include a load station 102 and an automated preparation station 104 for preparing the two ends of a length of optical fiber while is stored on a fiber storage spool. Such a spool could be, for example, a bulk storage spool or an actual fiber shipping spool. Shipping spool as used herein means a spool or reel containing a length of fiber and which is to be shipped to a customer. The system 100 may also include an optical time domain reflectrometer (OTDR) and optical dispersion test station 106, a glass geometry measurement and fiber cutoff wavelength test station 108, a fiber deflection and optical fiber coating geometry test station 110, a polarization modal dispersion (PMD) test station 112, a visual inspection station 114, and an unload station 116. While presently preferred optical fiber tests and test stations are disclosed herein, one skilled in the art will appreciate that the present invention may be utilized with fewer or additional tests and test stations, and should not be construed as limited to the tests and test stations shown and described herein. The automated measurement system 100 includes a conveyor system 118 for transporting the pallets 50 or 90 carrying spools 10 of optical fiber 12 from test station to test station. A local programmable logic controller (PLC) 121 controls the operation of the load station 102, the preparation stations 104, the visual inspection station 114, and the unload station 116. As described further below, additional local PLCs may be employed to control the operation of the other stations. A plurality of RF devices, discussed further below, adapted to read from and/or write to the RF tag 82 attached to the pallet 50 or 90, are located in a plurality of locations adjacent to the conveyor system 118. Instructions read from the RF tag 82 control the progress of the pallet 50 or 90 through the conveyor system 118 via the local PLCs.

To begin processing, the spool 10 is loaded onto the pallet 50 or 90 with the fiber ends 12a and 12b positioned such they are readily accessible to the individual test stations of system 100, as described above. As shown in FIG. 8, the spool is loaded onto the pallet 50 or 90 of the conveyor system 118 at the load station 102. The conveyor system 118 then moves the pallet 50 or 90 to the preparation station 104.

Figure 9:
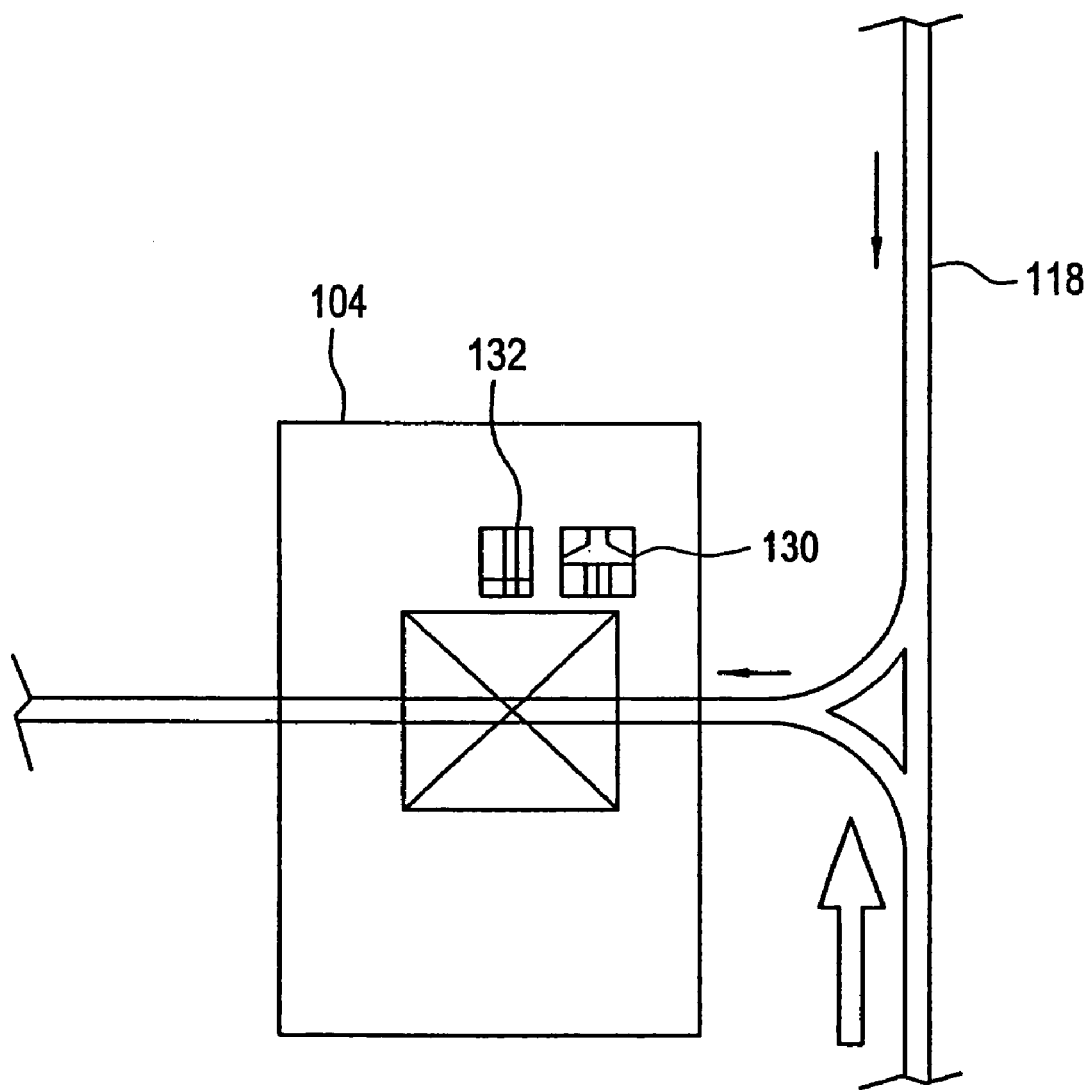
FIG. 9 shows a detailed view of a preparation station suitable for use in conjunction with the system of FIG. 8.

As seen in FIG. 9, the preparation station 104 includes a stripping device 130 for stripping the protective coating off of the optical fiber, and a cleaning device 132 for cleaning the fiber after the fiber coating has been stripped from the optical fiber. Both the stripping device and the cleaning device are preferably operated by pneumatic control techniques, and preferably the operation of these devices is under control of the local PLC 121 (shown in FIG. 8).

Additionally, the PLC 121 controls the movement of the pallet 50 or 90 while the pallet 50 or 90 is being processed by preparation station 104. After the PLC 121 has positioned the pallet 50 or 90 such that the end 12a is adjacent to the device 130, the stripping device 130 operates by initially moving below the end 12a and then rising up and positioning itself around end 12a. An auxiliary fiber clip (not shown) engages and securely holds the end 12a between the striping device 130 and the pallet 50 or 90. The stripping device 130 then closes around the end 12a and retracts in a direction away from the pallet to remove the coating 13 from the end 12a The stripping device also includes a fiber cutting device capable of performing a rough cut on the fiber to achieve a desired length of fiber extending from the feed finger assemblies. For example, in one embodiment, about 10 cm of fiber extends from the feed finger assemblies, about 5 cm of which is fiber whose protective coating has been removed. A vacuum nozzle then removes the coating debris into a central vacuum system.

The fiber stripping devices employed herein to remove the protective polymeric can be conventional fiber stripping devices, for example such as are available from the Miller Ripley Company, Miller Division, Cromwell, Conn., USA. Preferably the stripping devices employed herein are connected to pneumatic valves which may be computer controlled to control operation of the stripping devices. Fiber cutting can be achieved using conventional shears which are capable of performing a rough cut on the fiber.

The pallet 50 or 90 is then moved forward so that end 12a is adjacent to the cleaning device 132. The cleaning device 132 operates to remove any debris from the fiber end 12a. The device 132 includes a cleaning head, which may be, which includes a gripper mechanism having two arms with felt or sponge pads or alternatively, a polyurethane based open cell foam material. First, a needle squirts alcohol on to the pads to moisten them. Then the gripper advances forward onto the fiber end 12a and the alcohol dampened pads close onto the fiber end 12a The gripper then pulls back away from the pallet 50 or 90, thereby cleaning the fiber end 12a Preferably, the gripper is then rotated 90 degrees and the cleaning cycle is performed again.

The PLC 121 then positions the pallet 50 or 90 such that the end 12b is adjacent to the stripping device 130. The stripping, cutting, and cleaning process is then repeated for the end 12b. Alternatively, the coating 13 could be removed and the optical fiber cleaned by manual techniques. Preferably, the stripping and cutting device 130 and the cleaning device 132 are positioned so that, when one end of fiber is being stripped and cut to a desired length, the another end of fiber may be being cleaned. The automatic stripping, cutting and cleaning station is significant in that, for the first time, a fiber may be automatically prepared for testing, including removal of the protective polymeric coating and cutting of the end of the fiber, without any manual interaction from an operator.

Figure 10A:
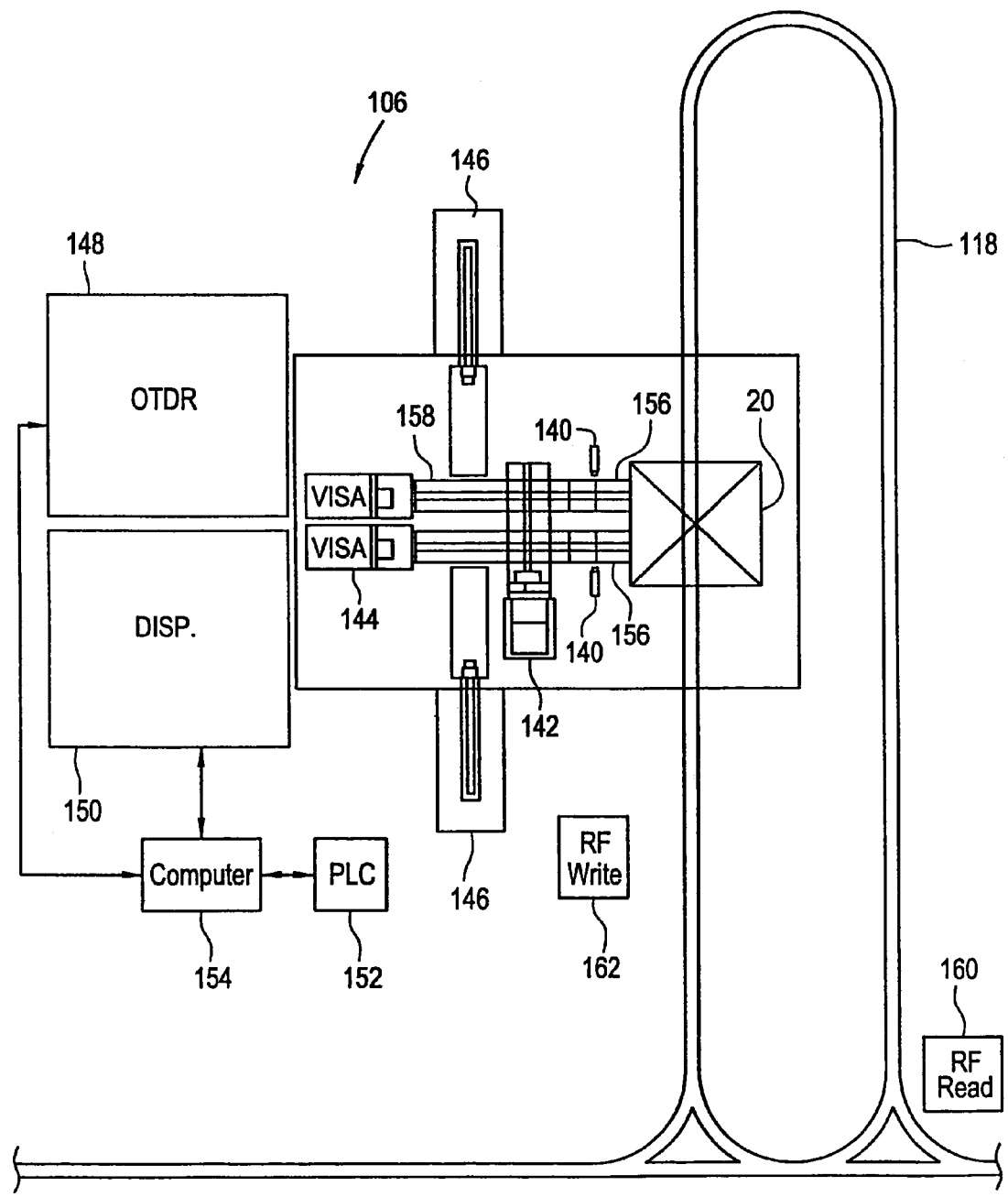
FIG. 10A shows a detailed view of an optical time domain reflectometry and optical dispersion test station suitable for use in conjunction with the system of FIG. 8.
Figure 10B:
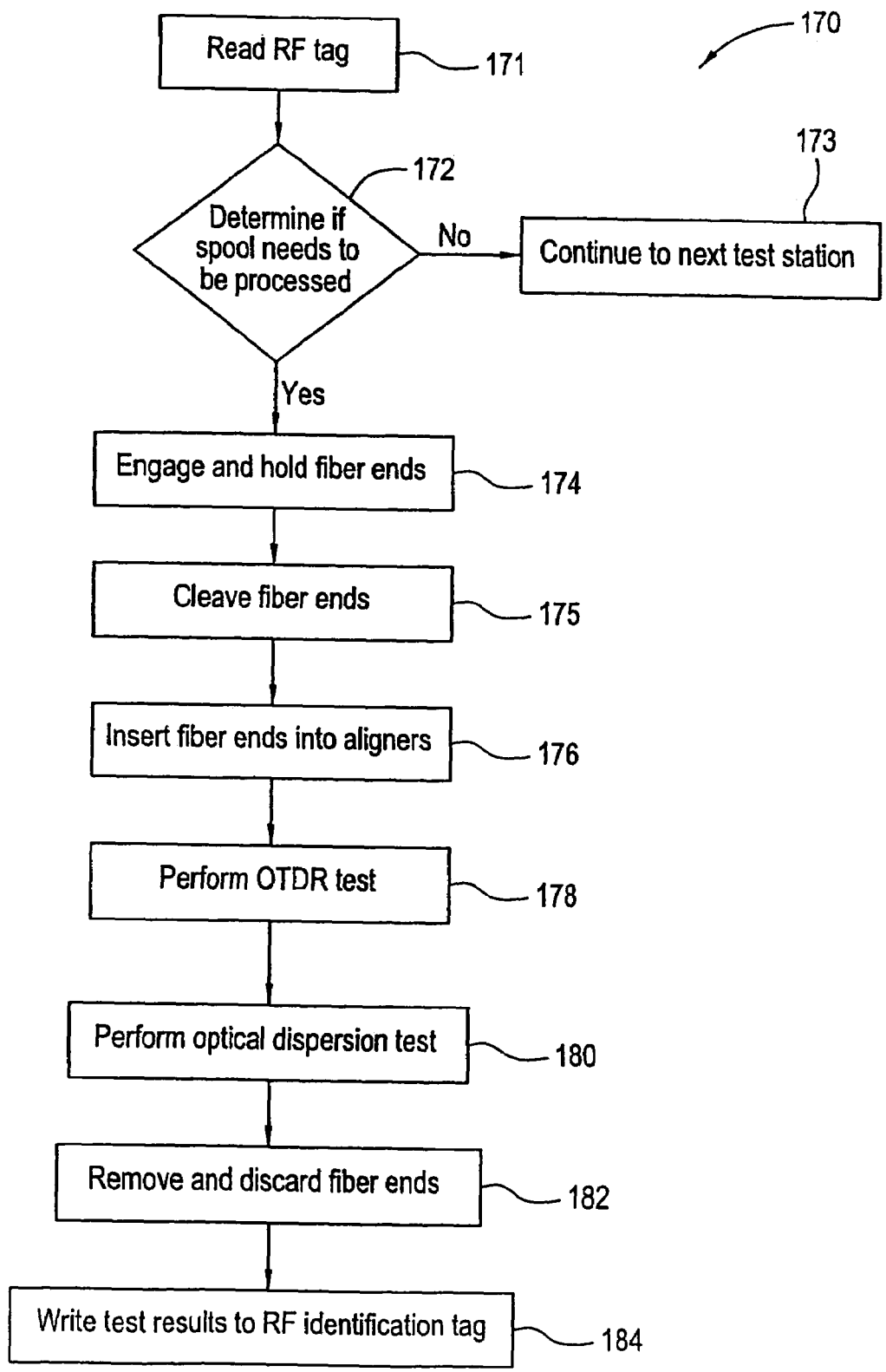
FIG. 10B is a flowchart of a method for automating the performance of the optical time domain reflectometry and the optical dispersion tests of FIG. 10A in accordance with the present invention.

In the embodiment illustrated in FIG. 8, after an appropriate length of each fiber end 12A and 12b has been stripped, cut, and cleaned, the pallet 50 or 90 is transported to test station 106. Alternatively, however, the pallet could be transported to an alternative test station if desired. As shown in FIG. 10A, the OTDR and optical dispersion test station 106 includes cutting devices 140, a cleaving device 142, fiber aligners 144, and fiber discarding devices 146. One fiber aligner 144 suitable for use with the present invention is the Model 1100 Single Fiber Aligner (PK Technology Inc., Beaverton, Oreg. 97008). The test station 106 includes an OTDR test machine 148 and an optical dispersion test machine 150, both optically coupled to the fiber aligners 144 and controlled by one or more computers 154. The test station 106 also includes a local PLC 152 communicatively connected to the computer 154, an RF tag reading device 160, and an RF tag writing device 162. A pair of fiber clips 156 are mounted on a servo slide 158 and controlled by the local PLC 152. Operation of the test station 106, including the computer 154, is controlled by the local PLC 152. FIG. 10B illustrates aspects of a method 170 of automating the performance of the OTDR and optical dispersion tests utilizing the test station 106 shown in FIG. 10A. In a first step 171, the RF tag reading device 160 reads the RF identification tag 52, determining routing instructions and processing instructions for the spool 10. In a second step 172, the PLC determines if the routing instructions indicate that the spool 10 should be processed by the test station 106. If the local PLC 152 determines that the spool is not to be processed by the test station 106, the pallet 50 or 90 is moved to the next test station in step 173. If the local PLC 152 determines the spool is to be processed by the test station 106, the pallet 50 or 90 is moved into position adjacent to the servo slide 158 in step 174, as shown in FIG. 10A. Clips 156 are provided to grip the ends of the fiber. Suitable clips for use as clips 156 can be so called Optical Fiber Clips which are available from EG&G Fiber Optics, Wokingham, Berge, United Kingdom, or Optical Fiber Clips which are also available from PK Technologies Inc., Beaverton Oreg., USA. The fiber clips 156 preferably have a V-shaped groove therein parallel to the direction the fiber will be inserted into the clip, and into which the fiber is grasped by the clip. The opening and closing of the clips is preferably controlled using pneumatic control methods. The clips 156 are moved by the servo slide 158 to the ends 12a and 12b where the clips 156 engage and hold the optical fiber ends 12a and 12b. In step 175, the servo slide 158 moves the clips 156 holding the fiber ends to the cleaving device 142 where the fiber ends 12a, 12b may be cleaved, or precision cut, leaving a predetermined length of optical fiber 12 protruding from each clip 156. The cleaving device preferably is capable of cleaving the fiber in a manner which results in a cleaved surface suitable for optical coupling, for example to one of the testing apparatus described herein. Such cleaving can be accomplished using optical fiber cleaving devices such as are available from Seimens in Germany. These fiber cutting devices are preferably also adapted to be controllable by pneumatic computer controlled devices. After an optical quality cleave has been made, in step 176 the servo slide 158 moves the clips 156 toward the fiber aligners 144, inserting an appropriate length of the fiber ends 12a, 12b into the fiber aligners 144.

Next, in step 178, the computer 154 commands the OTDR test machine 148, which is optically connected to the fiber aligners 144 as described above, to test the optical fiber 12. The OTDR test machine 148 provides a measure of the fiber attenuation of the optical fiber 12 over a selected wavelength range. OTDR attenuation measurements are made at a plurality of wavelengths which are within a predetermined selected range. The measured attenuations are analyzed to produce a curve representing attenuation, i.e., spectral attenuation, for the wavelengths of the selected range.

Next, in step 180, the computer 154 commands the optical dispersion test machine 150, which is also optically connected to the fiber aligners 144 as described above, to test the optical fiber 12. The optical dispersion test provides a measure of the distortion of optical signals as they propagate down optical fiber 12. Next, in step 182, the fiber discarding devices 146 engage and grasp the ends 12a and 12b of the optical fiber, the cutting devices 156 cut the stripped ends 12a and 12b of the optical fiber 12, and the fiber discarding devices 146 remove the pieces of optical fiber which were severed from the testing area. The fiber discarding devices 146 utilize a gripper mounted on a rod to grip the severed pieces of optical fiber and move them into a scrap trough.

Alternatively, the scrap fiber can be removed via a vacuum which is mounted or movable to a position which is close enough to remove the scrap fiber. Next, in step 184, the RF tag writing device 162 preferably writes the results of the OTDR and optical dispersion tests to the RF identification tag 52. The conveyor 118 then transports the pallet 50 or 90 to the next test station.

Figure 11A:
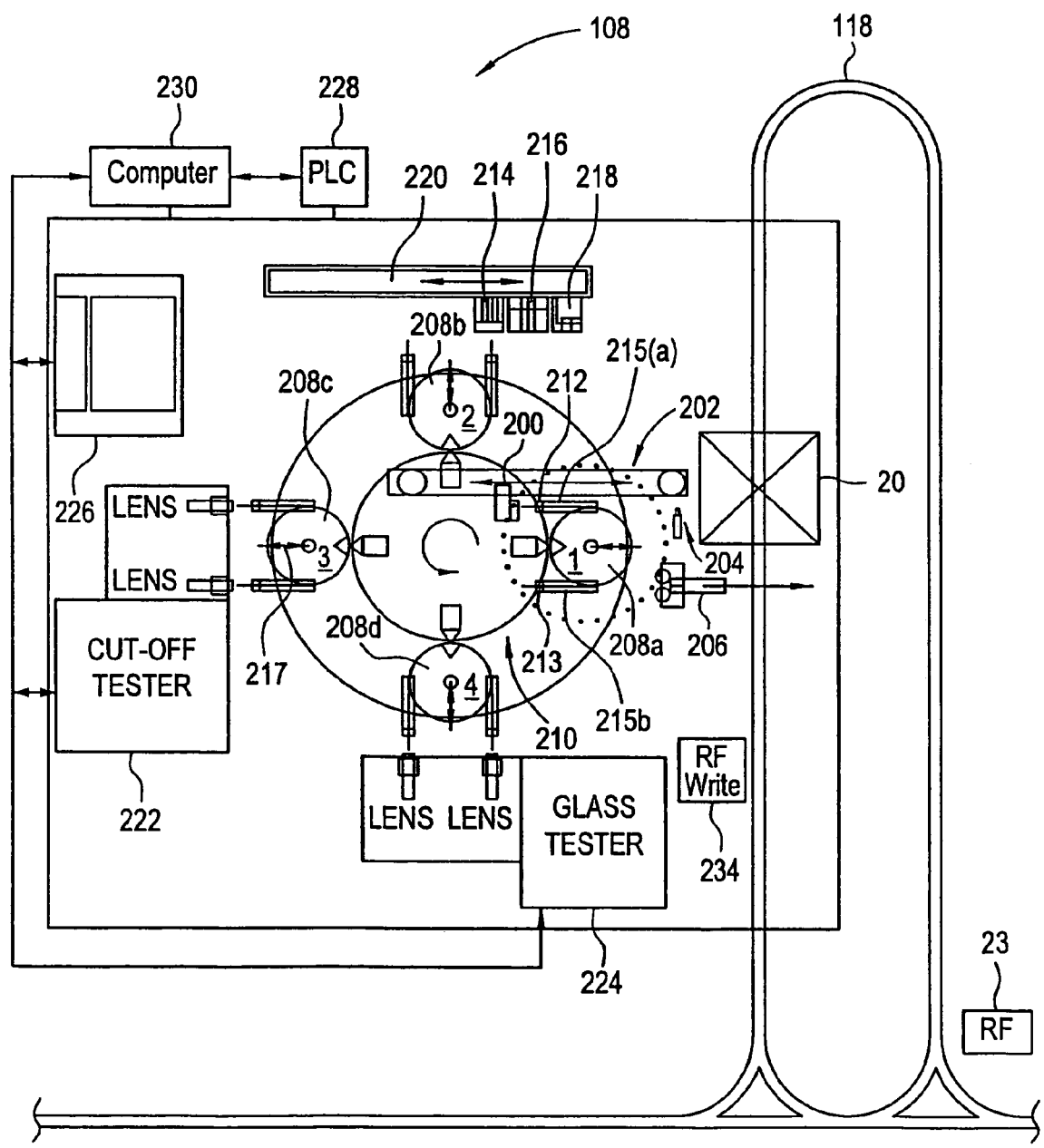
FIG. 11A shows a detailed view of a glass measurement and cutoff wavelength test station suitable for use in conjunction with the system of FIG. 8.

As shown in FIG. 11A, the glass geometry measurement and cutoff wavelength test station 108 includes a fiber clip 200 attached to a deployment slide 202, a cutting device 204, and a fiber discarding device 206. The test station 108 also includes mandrels 208a, 208b, 208c, 208d rotatably mounted on a dial plate 210. Mounted on each mandrel 208a, 208b, 208c, 208d are fiber gripping clips 212, 213 located at the ends of extension arms 215(*a*) and 215(*b*). A stripping device 214, a cleaning device 216, and cleaving device 218 are mounted on a slide 220. A cutoff wavelength tester 222 and a glass measurement tester 224 are communicatively connected to a vision alignment system 226. The test station 108 also includes an RF tag reading device 232 and an RF tag writing device 234. Operation of the test station 108, including one or more computers 230, is controlled by a local PLC 228.

Figure 11B:
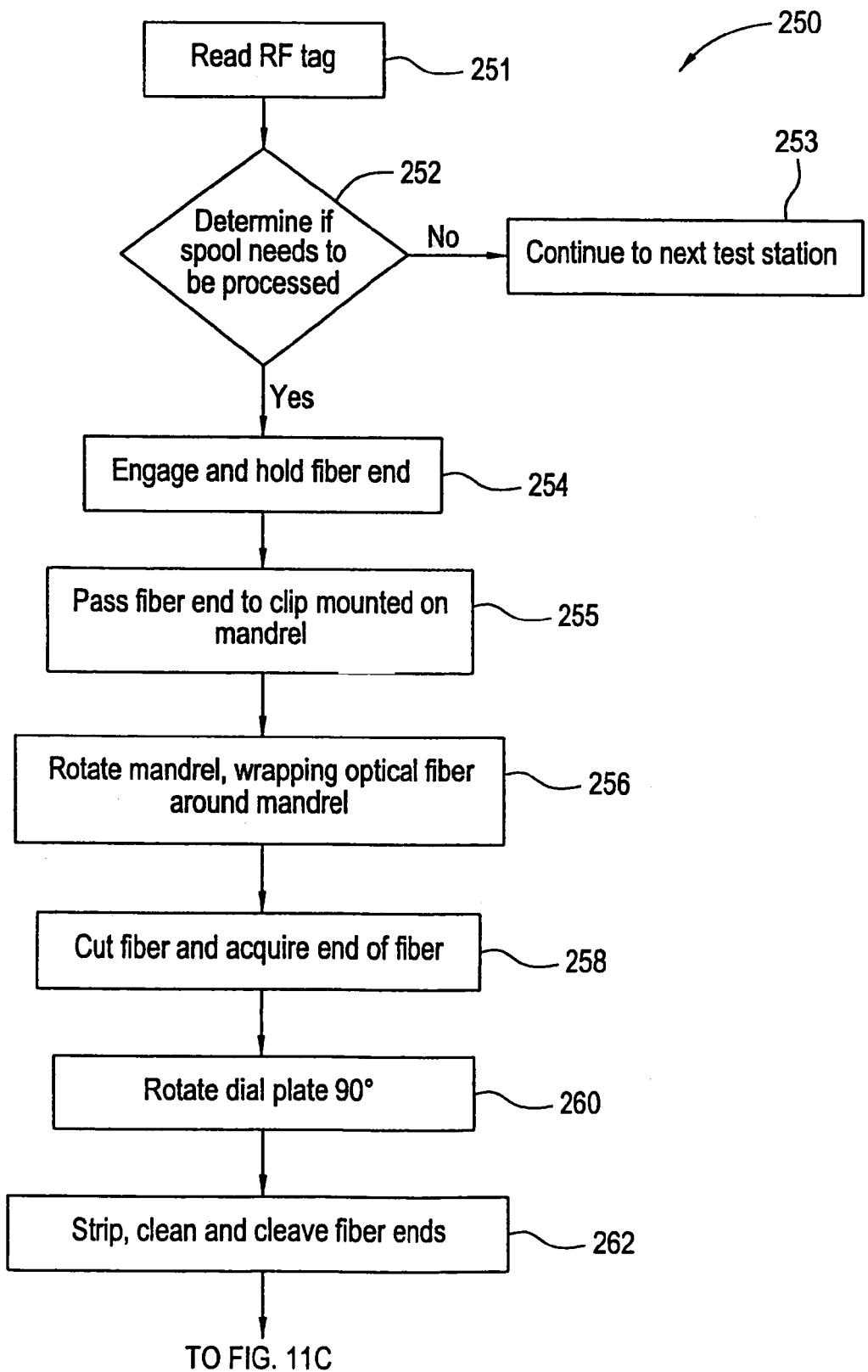
FIGS. 11B and 11C are a flowchart of a method for automating the performance of the glass measurement and cutoff frequency tests of FIG. 11A in accordance with the present invention.
Figure 11C:
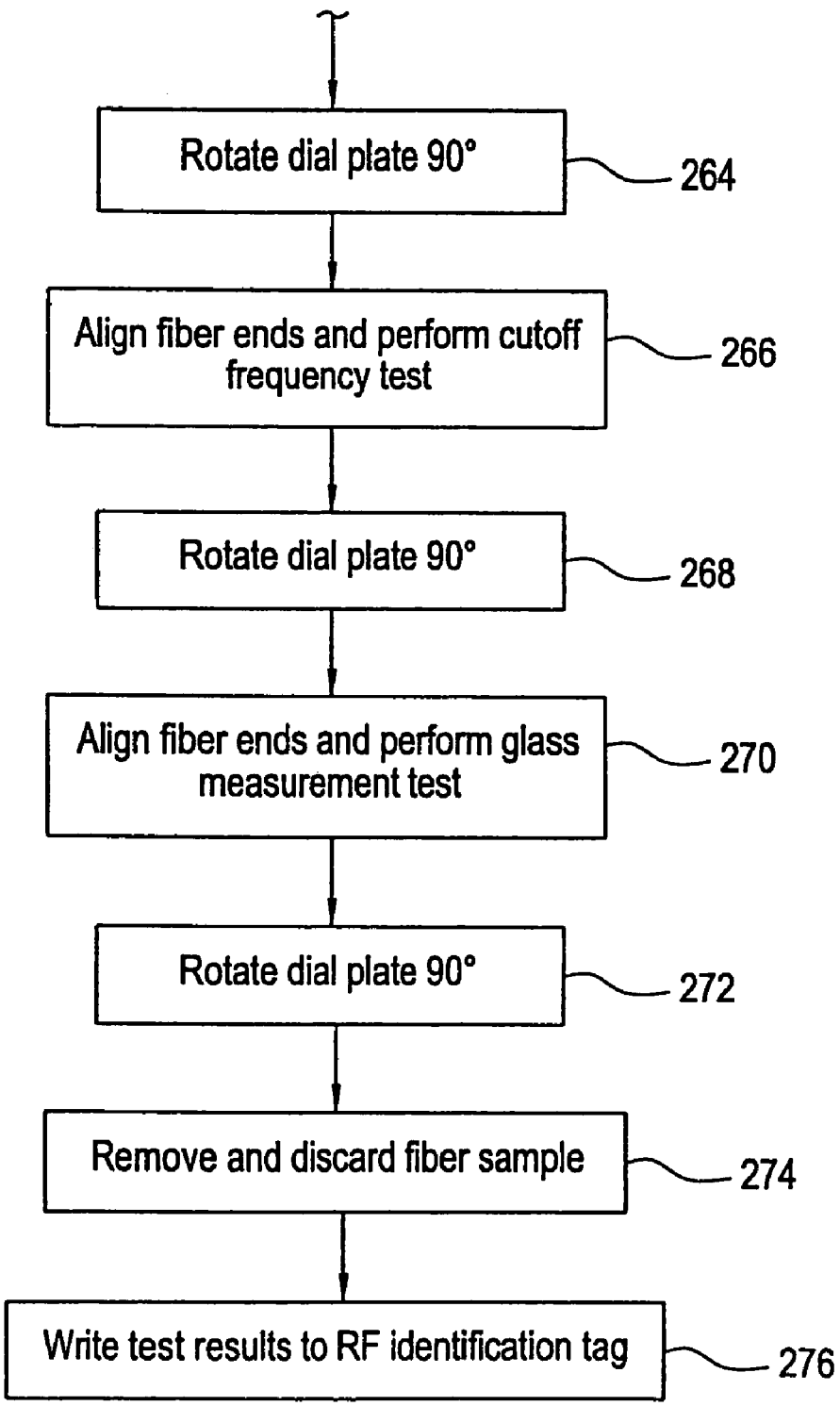

FIGS. 11B and 11C show a method 250 for automating the performance of the glass measurement and cutoff wavelength tests utilizing the test station 108 shown in FIG. 11A. In a first step 251, the RF tag reading device 232 reads the RF identification tag 52, determining routing instructions and processing instructions for the spool 10. In a second step 252, the local PLC 228 determines if the routing instructions indicate that the spool 10 should be processed by the test station 108. If the local PLC 228 determines that the spool 10 is not to be processed by the test station 108, the pallet 50 or 90 is moved to the next test station in step 253. If the local PLC 228 determines that the spool 10 is to be processed by the test station 108, the pallet 50 or 90 is moved into position adjacent to the slide 202 in step 254, as shown in FIG. 11A. The fiber clip 200 is moved by the deployment slide toward the spool 10, where the fiber clip 200 engages and grabs the fiber end 12a. The deployment slide 202 then moves the clip 200 away from the pallet 50 or 90, deploying a length of the optical fiber 12. In step 255, the fiber clip 200 passes the fiber end 12a to the fiber clip 212 mounted on the mandrel 208a. During this step, the fiber clip 200 moves laterally outward from slide 202 towards and into communication with clip 212 on mandrel extension arm 215(*a*). Next, in step 256, the mandrel 208a rotates counter-clockwise 1.5 rotations, wrapping approximately two meters of optical fiber 12 around the mandrel 208a, which is basically a cylinder having a diameter of about 11 inches, or 280 cm. During this step, a fiber guide ensures proper containment of the optical fiber 12 around mandrel 208(*a*) while the fiber is being wound onto the mandrel. Next, in step 258, the clip 213 attached to the mandrel 208a engages the optical fiber 12 and the cutting device 204 performs a cut on the optical fiber 12, leaving about two inches of fiber end exposed for testing. Thus, test station 108 has acquired a sample length of the optical fiber 12 which is wrapped around the mandrel 208 and held by the clips 212 and 213. Of course, this technique is not limited to use with an 11 inch diameter mandrel, and could be employed instead on mandrels having a different diameter, e.g. 3 inches.

In step 260, the dial plate 210 rotates 90° counter-clockwise, bringing the mandrel 208a adjacent to the slide 220. In next step 262, the fiber ends held by the clips 212, 213 are stripped of their plastic coating by stripping device 214, cleaned of excess debris by cleaning device 216, and cleaved by cleaving device 218, much the same as was described above with respect the stripping, cleaving, and cleaning station illustrated in FIG. 9. The stripping device 214, the cleaning device 216, and the cleaving device are movably mounted along the slide 220, and also are provided with transverse slides (not shown) which enable movement of these devices transverse to slide 220 to facilitate the stripping, cutting, and cleaning operations to the ends 12a and 12b. After these operations, in step 264, the dial plate 210 rotates 90° counter-clockwise, bringing the mandrel to face the cutoff wavelength tester 222, as illustrated by mandrel 208(*c*). Each of the rotatable mandrels are mounted on a slide located under the mandrel, which enables movement of the mandrel in the directions indicated by arrow 217. To interface the fiber ends 12a and 12b with cut-off tester 222, the entire mandrel 208(*c*) is moved towards cut-off tester to insert the fiber ends 12a and 12b into cut-off tester 222.

Next, in step 266, the PLC 228 commands the computer 230 to run the cutoff wavelength tester 222 to test the sample of optical fiber. In this step 266, the computer 230 directs the vision device 226 to align the lenses of the cutoff wavelength tester 222 with the fiber ends held by the clips 212 and 213. The computer 230 then directs the cutoff wavelength tester 222 to test the sample of optical fiber. The cutoff wavelength test determines the cutoff wavelength at which the optical fiber begins to operate like a single mode optical fiber.

Then, in step 268, the mandrel retracts back, pulling the fiber ends 12a and 12b out of cut-off tester, and dial plate 210 rotates 90° counter-clockwise, bringing the mandrel 208a adjacent to the glass measurement tester 224. In step 270, the PLC 228 commands the computer 230 to test the sample of optical fiber. In this step 270, the vision device 226 aligns the lenses of the glass measurement tester 224 with the fiber ends and the glass measurement tester 224 tests the optical fiber. The glass measurement tester 224 determines relative geometrical parameters of the core and clad portions of the optical fiber sample. Additionally, the glass measurement tester 224 may measure the core and clad concentricity.

As shown in step 272, the dial plate 210 rotates 90° counter-clockwise, bringing the mandrel 208a to face the pallet 50 or 90. Next, in step 274, the fiber discarding device 206 grips one of the fiber ends, the fiber clips 212, 213 release the fiber ends, and the fiber discarding device 206 removes and discards the optical fiber sample. Next, in step 276, the RF tag writing device 234 writes the results of cutoff wavelength and glass measurement tests to the RF identification tag 52. The conveyor 118 then transports the pallet 50 or 90 to the preparation station 104 before passing the pallet 50 or 90 to the next test station.

The four mandrels 208a, 208b, 208c, 208d advantageously allow four samples of optical fiber to be processed simultaneously, reducing equipment cost and improving throughput. While a first fiber sample is being acquired and wrapped around mandrel 208a, a second fiber sample wrapped around mandrel 208b may be being stripped, cleaned, and cleaved, a third fiber sample wrapped around mandrel 208c may be undergoing cutoff wavelength testing, and a fourth fiber sample wrapped around mandrel 208d may be undergoing glass measurement testing.

Figure 12A:
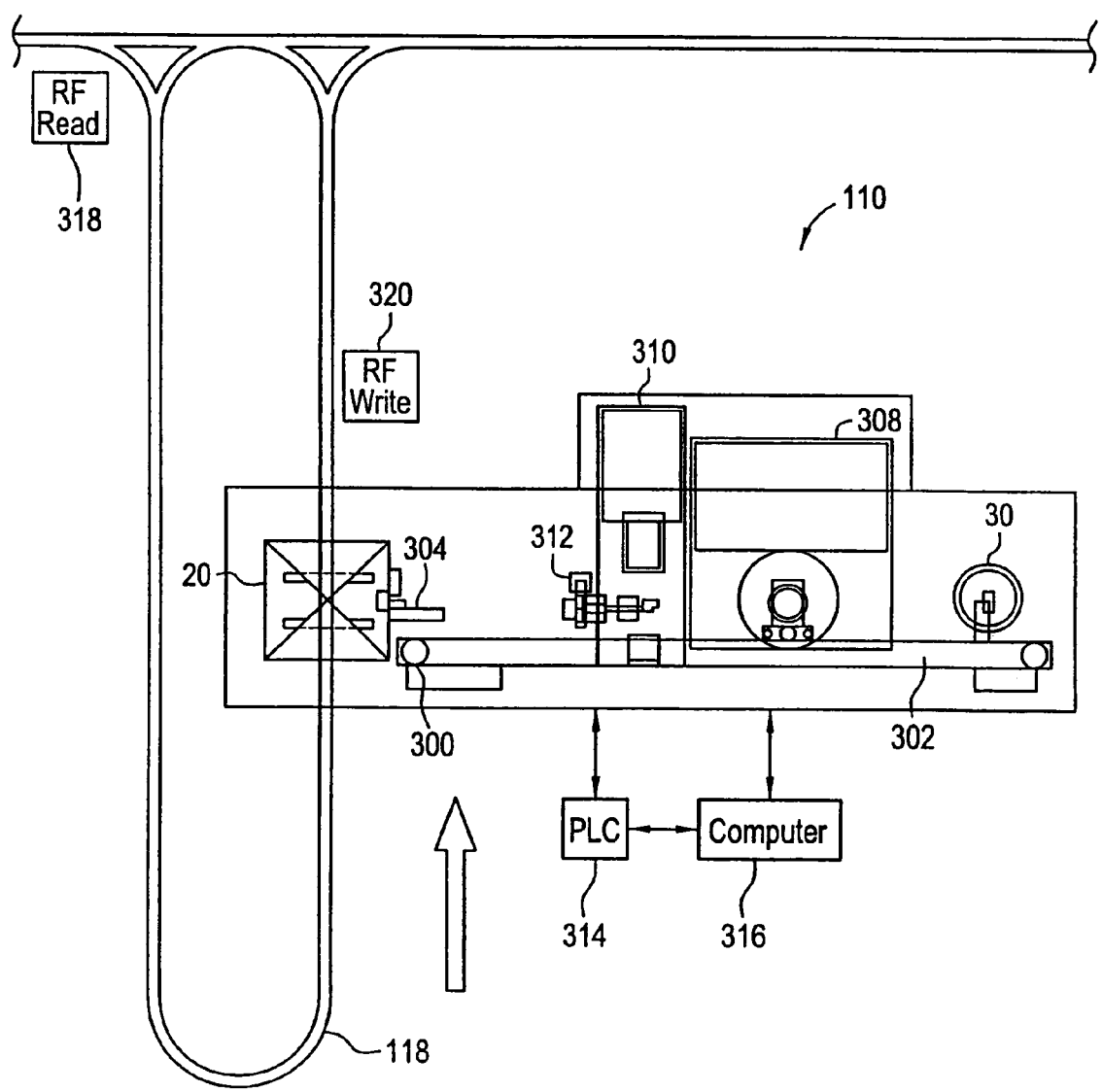
FIG. 12A shows a detailed view of a fiber deflection test station and coating geometry test station suitable for use in conjunction with the system of FIG. 8.

As shown in FIG. 12A, the fiber deflection and coating geometry test station 110 includes a fiber clip 300 attached to a deployment slide 302, a cutting device 304, a fiber discarding device 306, and a coating geometry tester 308. An optical fiber deflection tester 310 includes a spin drive 312. The test station 110 also includes an RF tag identification read device 318 and an RF tag identification write device 320. Operation of the test station 110, including one or more computers 316, is controlled by a local PLC 314.

According to a preferred embodiment of the present invention, two samples from each spool are processed simultaneously.

Figure 12B:
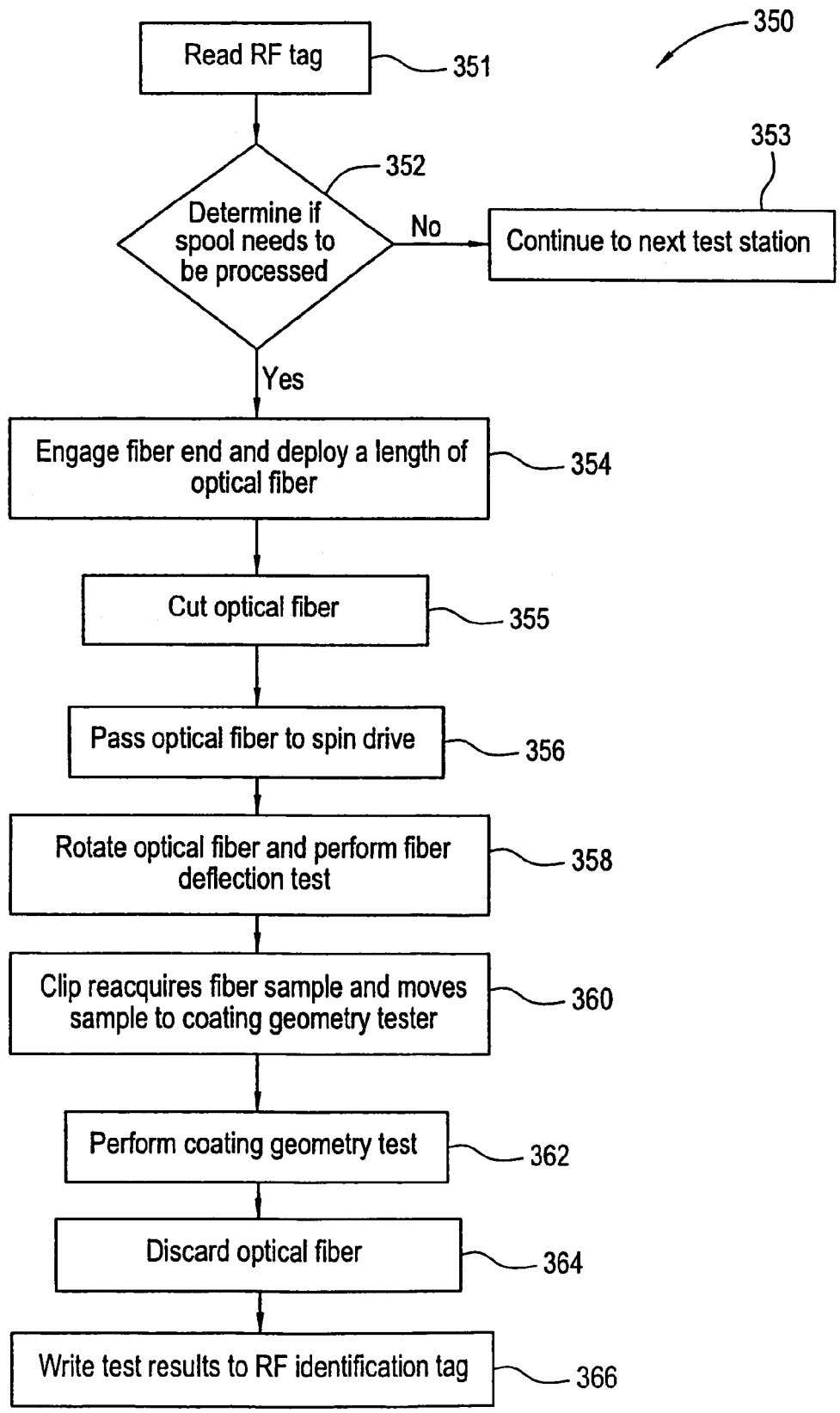
FIG. 12B is a flowchart of a method for automating the performance of the optical fiber deflection and coating geometry tests of FIG. 12A in accordance with the present invention.

FIG. 12B shows a method 350 for automating the performance of the fiber curl and coating geometry tests utilizing the test station 110 shown in FIG. 12A. In first step 351, the RF tag reading device 318 reads the RF identification tag 52, determining routing instructions and processing instructions for the spool 10. In a second step 352, the local PLC 314 determines if the routing instructions indicate that the spool 10 should be processed by the test station 110. If the local PLC 314 determines that the spool 10 is not to be processed by the test station 110, the pallet 50 or 90 is moved to the next test station in step 353. If the local PLC 314 determines the spool 10 is to be processed by the test station 110, the pallet 50 or 90 is moved into position adjacent to the slide 302 in step 354, as shown in FIG. 12A. The fiber clip 300 is moved by the deployment slide 302 toward the spool 10 where the clip 300 engages and holds the fiber end 12a. The deployment-slide 302 moves the clip 300 away from the pallet 50 or 90, deploying a length (e.g., 8 inches) of the optical fiber. In step 355, the cutting device 304 cuts the optical fiber, leaving a sample of the optical fiber held by the clip 300. In step 356, the fiber clip 300 moves along the slide 302 and passes the optical fiber sample to the spin drive 312 which holds the fiber sample by an end.

Next, in step 358, the PLC 314 commands the computer 316 to run the fiber curl tester 310. The optical fiber sample is rotated about its axis by the spin drive 312 while measurements of deflection versus a reference are periodically taken. From this data, a measurement of fiber curl is determined. In step 360, the clip 300 reacquires the sample from the spin drive 312 and slides the sample along the slide 302 to the coating geometry tester 308. In step 362, the fiber sample passes to a clamp or fiber gripping device which then rotates the sample of optical fiber into a vertical orientation and inserts it into the coating geometry tester 308. The PLC 314 commands the computer 316 to run the coating geometry tester 308. In this test, the fiber sample is placed vertically and rotated about its axis by the coating geometry tester 308 while data relative to coating and glass fiber geometry is measured. From this data, various parameters about the placement of the fiber within the coating are determined. Next, in step 364, the fiber sample is removed from the coating geometry tester 308 by the clamp and passed to the clip 300. The clip 300 moves the sample along the deployment slide 302 to the fiber discarding device 306 which acquires and discards the fiber sample. In step 366, the RF tag writing device 320 writes the results of coating geometry and fiber deflection tests to the RF identification tag 52. The conveyor 118 then transports the pallet 50 or 90 to the next test station.

Figure 13A:
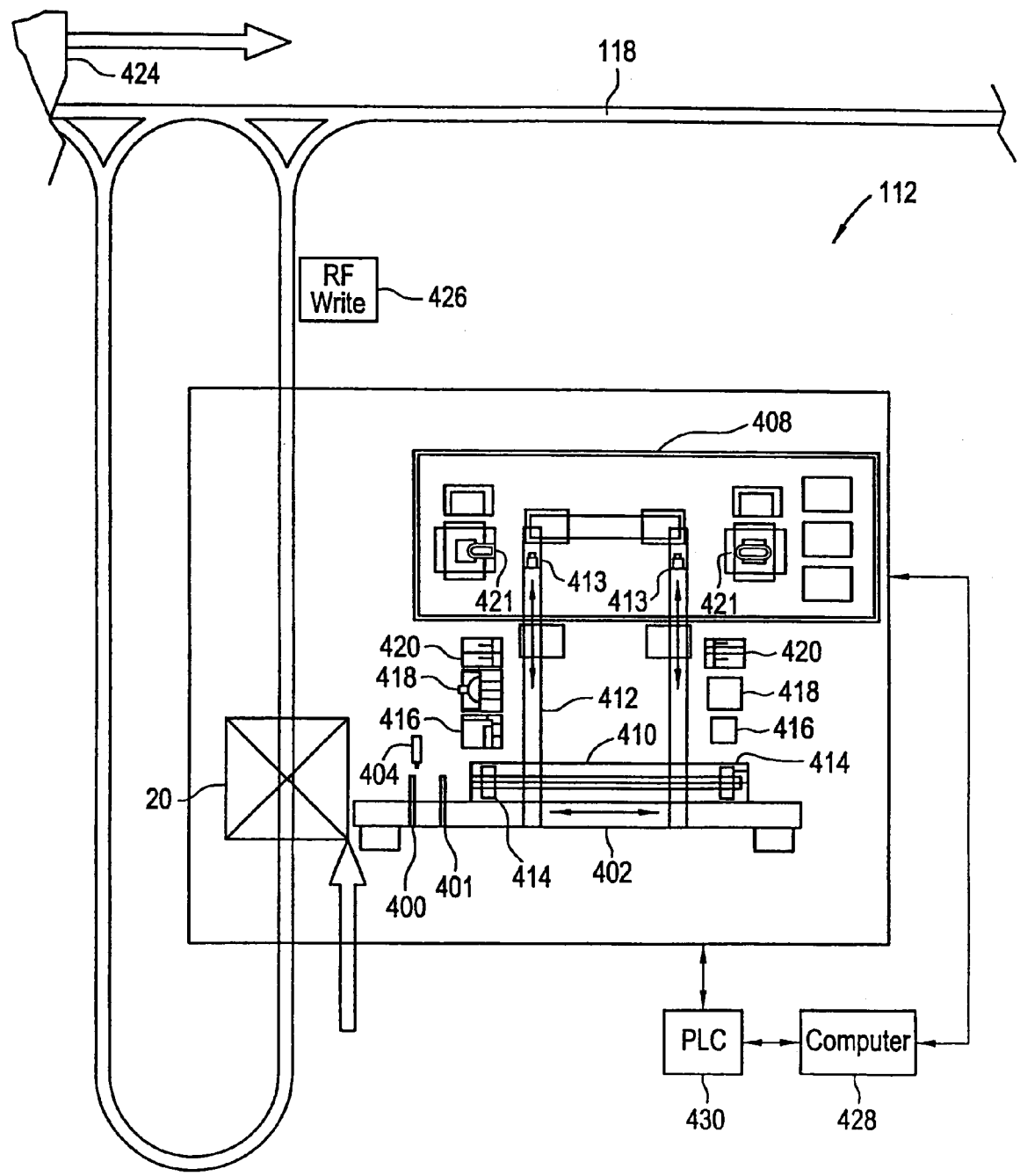
FIG. 13A shows a detailed view of a polarization modal dispersion test station suitable for use in conjunction with the system of FIG. 8.

As shown in FIG. 13A, the PMD test station 112 includes a fiber clip 400 and a gripper 401 attached to a deployment slide 402, a cutting device 404, and a PMD tester 408. A V-groove tool 410 with clips 414 is located adjacent to the deployment slide 402. The test station 112 also includes a transfer slide 412 with fiber clips 413. Stripping devices 416, cleaning devices 418, cleaving devices 420 are located adjacent to the transfer slide 412. The PMD tester 408 includes clips 421. The test station 112 also includes an RF tag identification reading device 424 and an RF tag identification writing device 426. Operation of the test station 112, including one or more computers 428, is controlled by a local PLC 430.

One exemplary type of PMD tester suitable for use with the present invention is described in U.S. Provisional Patent Application Ser. No. 60/127107, filed on Mar. 31, 1999, entitled "System and Method for Measuring Polarization Mode Dispersion Suitable for a Production Environment" which is incorporated by reference herein in its entirety.

Figure 13B:
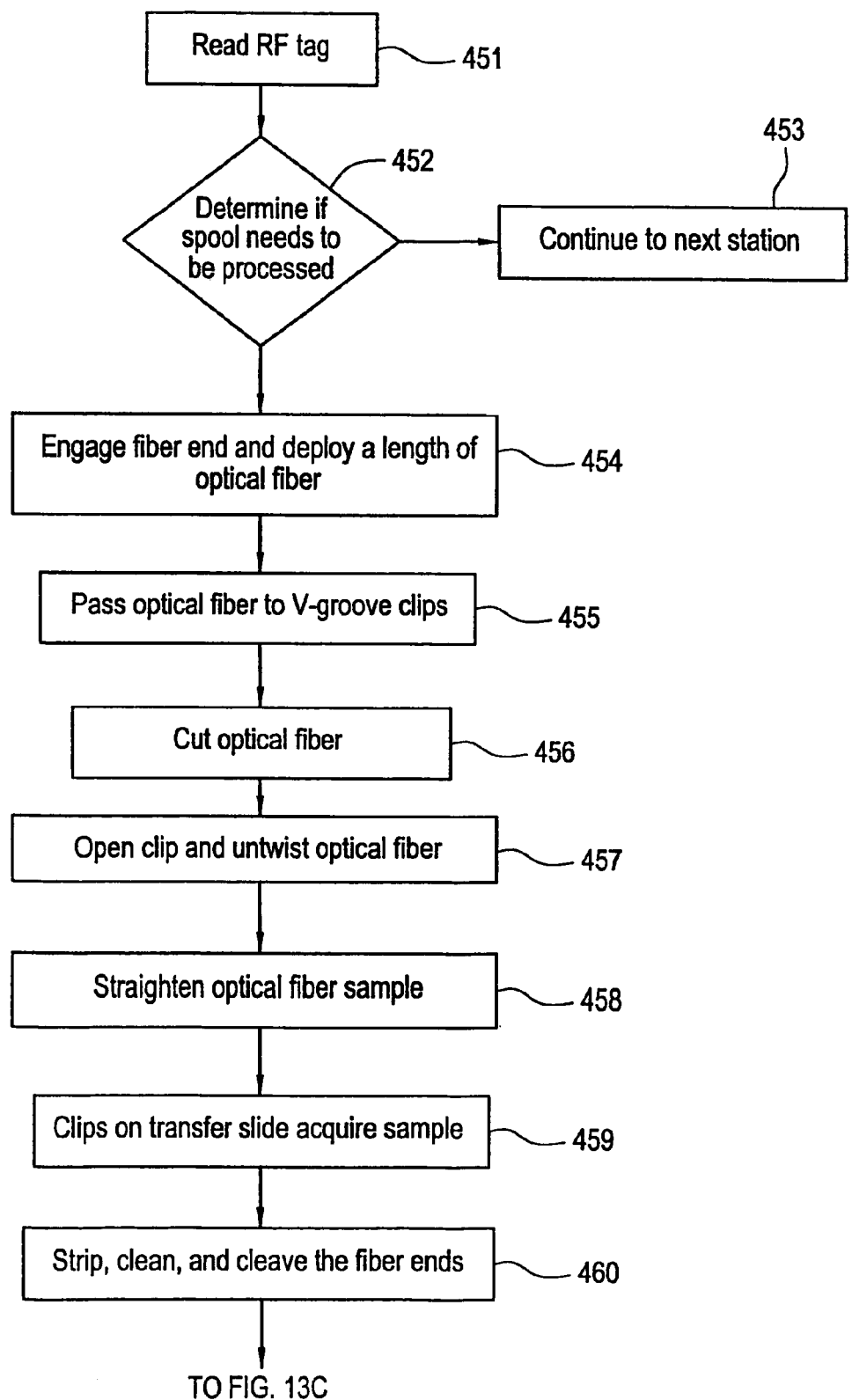
FIGS. 13B and 13C are a flowchart of a method for automating the performance of the polarization modal dispersion test of FIG. 13A in accordance with the present invention.
Figure 13C:
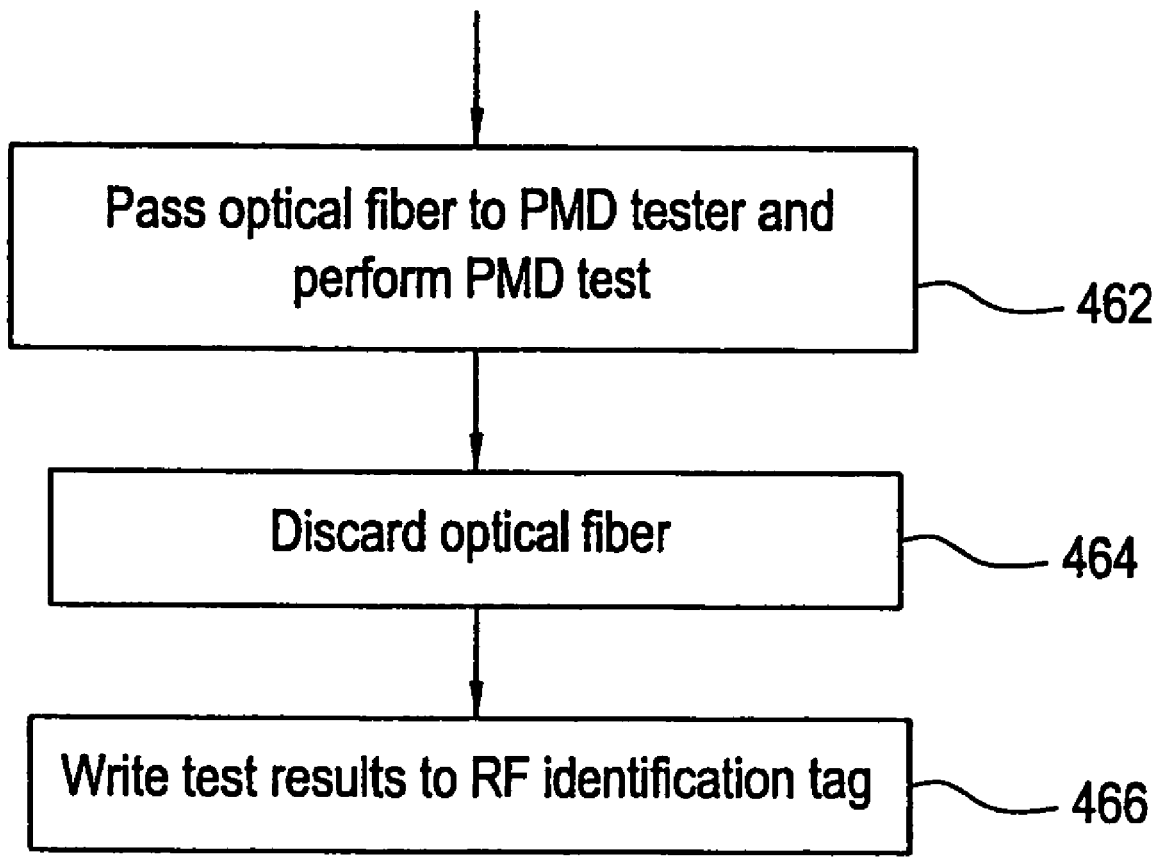

FIGS. 13B and 13C show a method 450 for automating the performance of the fiber PMD test utilizing the test station 112 shown in FIG. 13A. In a first step 451, the RF tag read device 424 reads the RF identification tag 52, determining routing instructions and processing instructions for the spool 10. In a second step 452, the local PLC 430 determines if the routing instructions indicate the spool 10 should be processed by the test station 112. If the local PLC 430 determines that the spool 10 is not to be processed by the test station 112, the pallet 50 or 90 is moved to the next station in a step 453. If the local PLC 430 determines the spool 10 is to be processed by the test station 112, the pallet 50 or 90 is moved into position adjacent to the slide 402 in step 454, as shown in FIG. 13A. The fiber clip 400 is moved by the slide 402 toward the spool 10 where the clip 400 engages and holds the fiber end 12a and the deployment slide 402 moves the clip 400 away from the pallet 50 or 90, deploying a length (e.g., 12 inches) of the optical fiber 12 above the V-groove of the V-groove tool 410. In step 455, the clips 414 of the V-groove tool 410 elevate and acquire the optical fiber as the clip 400 releases it. In step 456, the cutting device 404 cuts the optical fiber, leaving a sample of the optical fiber held by the clips 414. In step 457, the clips 414 lower the optical fiber sample to the bottom of the V-groove and the clip 414 closest to the conveyor 118 is released. Also in the step 457, air is forced through holes in the bottom of the V-groove, creating a bed of air which will allow the optical fiber sample to use its own torsional flex to unwind to an untwisted state. In step 458, the felt-tipped gripper 401 attached to the slide 402 lowers and clamps the fiber sample at the end held by the clip 414. The gripper 401 then moves along the length of the sample to straighten it. The clip 414 which had previously released the optical fiber sample in the step 457 reacquires the sample.

Next, in step 459, the clips 413 move along slide 412 to the V-groove and acquire the fiber sample from the clips 414. After acquiring the sample, the clips move slightly towards each other, allowing a small amount of sag to develop in the optical fiber sample. In step 460, the clips 413 move the sample along the slide 412 where the ends of the optical fiber sample are stripped by stripping devices 416, cleaned by the cleaning devices 418, and cleaved by the cleaving devices 420. In step 461, the clips 413 move along slide 412 and pass the sample to the clips 421 of the PMD tester 408 which tests the optical fiber sample. In step 464, the sample of optical fiber is discarded by the discarding device 406. In step 466, the RF tag writing device 426 writes the results of PMD test to the RF identification tag 52. The conveyor 118 then transports the pallet 50 or 90 to the next station.

At the visual inspection station 114 shown in FIG. 8, an operator manually inspects the spool 10 at the visual inspection station 114. The local PLC 121 routes the pallet 50 or 90 to the inspection station 114 after the spool 10 has passed all of the tests described above. In addition to inspecting the spool 10, the operator tapes the optical fiber ends 12a, 12b to the spool 10. When the pallet 50 or 90 leaves the visual inspection station 114, an RF tag reading device 115 reads the RF identification 52 and transmits the test results to the manufacturing line, allowing the manufacturing process to be adjusted with timely feedback from the system 100. The conveyor 118 the transports the pallet 50 or 90 to the unload station 116.

Figure 14:
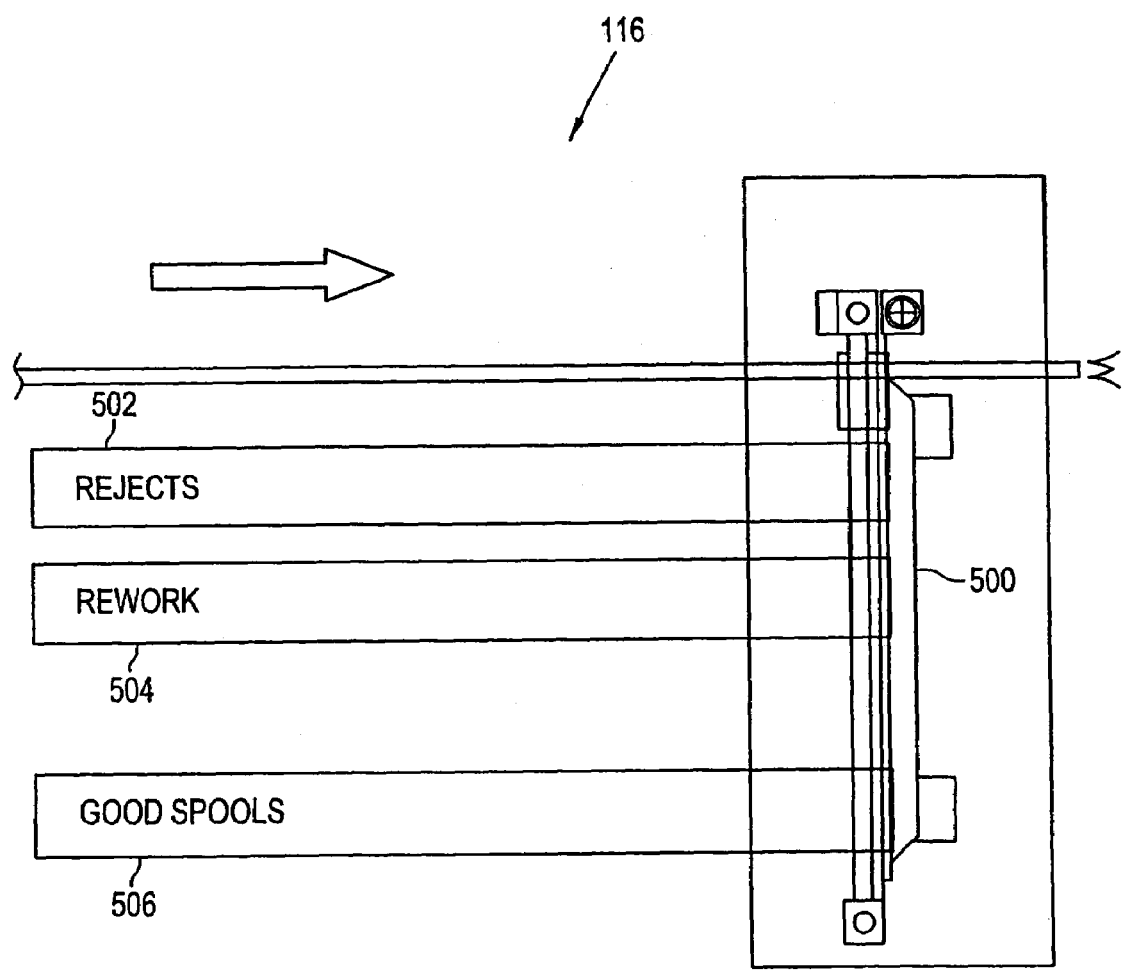
FIG. 14 shows a detailed view of an unload station suitable for use in conjunction with the system of FIG. 8.

As shown in FIG. 14, the unload station 116 includes an unload device 500, a reject queue 502, a rework queue 504, and a passed queue 506. The local PLC 121 routes the pallet 50 or 90 to the unload station 116 after the spool 10 has been manually inspected or has failed one of the tests described above. When the pallet 50 or 90 reaches the station 116, the PLC 121 directs the unload device 500 to remove the spool 10 from the pallet 50 or 90 and place the spool in the appropriate queue. The empty pallet 50 or 90 then proceeds to the load station where another spool is loaded.

It will be apparent to those skilled in the art that various modifications and variations can be made in the present invention without departing from the spirit and scope of the present invention. Thus, it is intended that the present invention cover the modifications and variations of this invention provided they come within the scope of the appended claims and their equivalents.

What is claimed is:

1. A pallet adapted for carrying a spool of optical fiber comprising:
   a mounting device adapted for holding a spool of optical fiber;
   a first structure adapted for holding a first end of the optical fiber such that the first end of the optical fiber extends outward in a such a manner as to provide easy access to the first end; a second structure adapted for holding a second end of the optical fiber such that the second end of the optical fiber extends outward in a such a manner as to provide easy access to the second end; wherein the first structure is further adapted to allow optical fiber to be unwound from the first end without disturbing the second end of the optical fiber; and
   the second structure is further adapted to allow optical fiber to be unwound from the second end without disturbing the first end.

2. The pallet of claim 1 wherein:
   the first structure and the second structure are further adapted to allow optical fiber to be unwound from both the first end and the second end simultaneously.

3. The pallet of claim 1 wherein the pallet is further adapted for carrying the spool of optical fiber to an optical fiber test station.

4. The pallet of claim 1 wherein the pallet is further adapted for use with an automated optical fiber test system.

5. The pallet of claim 1 wherein the pallet is further adapted for use with a conveyor system to carry the spool of optical fiber from a first automated test station to second automated test station.

6. The pallet of claim 1 further comprising:
   a data storage device attached to the pallet adapted to be read from and written to.

7. The pallet of claim 6 wherein the data storage device identifies the spool of optical fiber and provides a database of at least one test result.

8. A pallet adapted for carrying a spool of optical fiber comprising:
   a base;
   a spool holding apparatus mounted on the base adapted for holding the spool of optical fiber;
   a first feed finger assembly attached to the base adapted for holding a first end of the optical fiber;
   a second feed finger assembly attached to the base adapted for holding the second end of the optical fiber;
   wherein the pallet is adapted to allow optical fiber to be unwound from the first end without disturbing a second end of the optical fiber, and to allow optical fiber to be unwound from the second end without disturbing the first end.

9. A pallet adapted for carrying a spool of optical fiber comprising:
   a base;
   a spool holding apparatus mounted on the base adapted for holding the spool of optical fiber;
   a first vertical bracket mounted to the base;
   a second vertical bracket mounted to the base;
   a first feed finger assembly rotationally mounted to the first vertical bracket adapted for holding a first end of the optical fiber and allowing optical fiber to be unwound from the first end without disturbing a second end of the optical fiber; and
   a second feed finger assembly mounted to the second vertical bracket adapted for holding the second end of the optical fiber and allowing optical fiber to be unwound from the second end without disturbing the first end.

10. The pallet of claim 9 wherein the spool carrying apparatus comprises a roller assembly including a pair of rollers.

11. The pallet of claim 9 further comprising:
    a pickoff assembly rotationally mounted on the first vertical bracket;
    a first lead meter including an eyelet extending from the pickoff assembly adapted to contain the optical fiber;
    a clutch assembly mounted on the pickoff assembly adapted to engage the spool such that when optical fiber is unwound from the second end, the pickoff assembly, the first lead meter, and the clutch assembly rotate in synchronization with the spool, and when optical fiber is unwound from the second end, the spool remains substantially stationary and the pickoff assembly, the first lead meter, and the clutch assembly rotate.

12. The pallet of claim 11 further comprising:
    an upright guide roller mounted on the base adapted to guide the optical fiber; a secondary roller attached to the second vertical bracket adapted to guide the optical fiber; and
    a second lead meter including a second eyelet extending from the second vertical bracket adapted to contain the optical fiber.

* * * * *